(12) United States Patent
Bigot et al.

(10) Patent No.: US 7,265,111 B2
(45) Date of Patent: Sep. 4, 2007

(54) ADENOSINE ANALOGUES AND THEIR USE AS PHARMACEUTICAL AGENTS

(75) Inventors: Antony Bigot, Vitry-sur-Seine (FR); Siegfried Stengelin, Frankfurt am Main (DE); Gerhard Jaehne, Frankfurt am Main (DE); Andreas Herling, Bad Camberg (DE); Guenter Mueller, Sulzbach (DE); Franz Jakob Hock, Dieburg (DE); Michael R Myers, Fishers, IN (US)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 579 days.

(21) Appl. No.: 10/608,689

(22) Filed: Jun. 27, 2003

(65) Prior Publication Data

US 2004/0127434 A1 Jul. 1, 2004

Related U.S. Application Data

(60) Provisional application No. 60/434,164, filed on Dec. 17, 2002.

(30) Foreign Application Priority Data

Jun. 27, 2002 (EP) .................................. 02014324

(51) Int. Cl.
C07D 473/34 (2006.01)
C07D 471/04 (2006.01)
A61K 31/52 (2006.01)
A61P 3/10 (2006.01)
A61P 3/06 (2006.01)

(52) U.S. Cl. .............................. 514/234.2; 514/263.4; 514/46; 536/27.3; 536/27.62; 544/118; 544/277

(58) Field of Classification Search ............... 536/27.3, 536/27.62; 544/118, 277; 514/234.2, 46, 514/263.4
See application file for complete search history.

(56) References Cited

U.S. PATENT DOCUMENTS

| 4,755,594 | A | * | 7/1988 | Bridges et al. ............ 536/27.62 |
| 5,364,862 | A | | 11/1994 | Spada et al. |
| 5,561,134 | A | | 10/1996 | Spada et al. |
| 5,652,366 | A | | 7/1997 | Spada et al. |
| 5,736,554 | A | | 4/1998 | Spada et al. |
| 6,376,472 | B1 | | 4/2002 | Myers et al. |
| 6,407,076 | B1 | * | 6/2002 | Box et al. ............ 514/46 |
| 6,455,510 | B1 | * | 9/2002 | Charles et al. ............ 514/46 |
| 6,559,313 | B2 | | 5/2003 | Myers et al. |
| 2006/0009417 | A1 | * | 1/2006 | Elzein et al. ............ 514/46 |
| 2006/0052330 | A1 | * | 3/2006 | Zablocki et al. ............ 514/45 |

FOREIGN PATENT DOCUMENTS

| EP | 0181129 | 5/1986 |
| GB | 1101108 | 1/1968 |
| WO | WO88/03147 | 5/1988 |
| WO | WO95/07921 | 3/1995 |
| WO | WO97/33591 | 9/1997 |
| WO | WO99/24449 | 5/1999 |
| WO | WO99/24450 | 5/1999 |

OTHER PUBLICATIONS

Saltiel, A.R., et. al., The Molecular and Physiological Basis of Insulin Resistance: Emerging Implications for Metabolic and Cardiovascular Diseases, The Journal of Clinical Investigation (2000) vol. 106, No. 2 pp. 163-164.

* cited by examiner

*Primary Examiner*—Mark L. Berch
(74) *Attorney, Agent, or Firm*—Barbara E. Kurys

(57) ABSTRACT

The present invention relates to compounds according to the general formula (I)

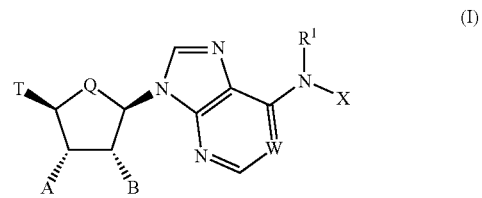

(I)

wherein X is selected from the group consisting of

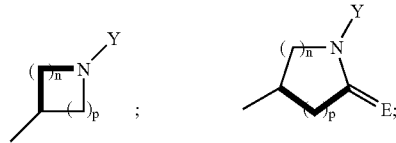

wherein n and p are independently 0, 1, 2, or 3, provided that n+p is a least 1;
and unsubstituted and at least monosubstituted $C_1$-$C_{10}$-alkylene-Y, $C_2$-$C_{10}$-alkylene-Y, $C_3$-$C_{10}$-cycloalkylene-Y and $C_3$-$C_{10}$-cycloalkenylene-Y; and
$R^1$, A, B, Q, T, Y, E and W have the meanings given in the description.

These compounds are useful for the manufacture of a medicament for the treatment of insulin resistance, type 2 diabetes, metabolic syndrome, lipid disorders or cardiovasular disease or for providing an anti-lipolytic effect.

14 Claims, No Drawings

ADENOSINE ANALOGUES AND THEIR USE AS PHARMACEUTICAL AGENTS

The present invention relates to compounds derived from adenosine and analogues thereof according to the general formula (I), with the definitions of $R^1$, A, B, Q, T, W and X given below in the text, and their use as pharmaceutical agents.

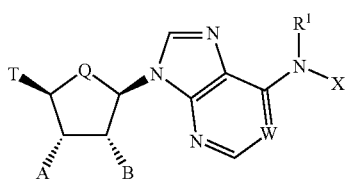

The invention furthermore relates to intermediates of compounds according to the general formula (III), as defined in the specification.

The physiological and pharmacological actions of adenosine and analogues are mediated through specific receptors located on cell surfaces. Four adenosine receptor subtypes, designated as $A_1$, $A_{2A}$, $A_{2B}$, and $A_3$ receptors, have been identified. Several potent metabolically-stable analogues of adenosine have been synthesized which demonstrate varying degrees of selectivity for the receptor subtypes.

There exists are huge number of adenosine analogues having a wide variety of physiological and pharmacological actions including a marked alteration of cardiovascular, renal and fat cell function.

For example, adenosine derivatives useful as anti-hypertensive, cardioprotective, anti-ischemic and antilipolytic agents are known from U.S. Pat. No. 5,561,134, WO 98/01426 and WO 00/23447. Such adenosine derivatives do not have any substituents, which contain halogen and are attached to the tetrahydrofuran or cyclopentane fragments, respectively, in contrast to compounds according to the present invention.

Adenosine derivatives having substituents containing halogen and said substituents being attached to the tetrahydrofuran fragments according to the general formula (II) are disclosed by WO 99/24449 and WO 99/24450.

Said compounds can be employed, for instance, as inhibitors of lipolysis, as cardioprotective agents or they may be of value in the therapy of diabetes.

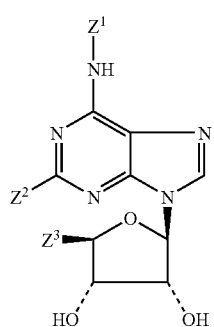

Unless indicated otherwise, the substituents of the above formula are defined for both WO 99/24449 and WO 99/24450 as follows:

Besides three further alternatives (4-6) which will not be specified below, $Z^1$ represents a group selected from (1) -(alk)$_n$-(C$_{3-7}$)cycloalkyl, including bridged cycloalkyl, said cycloalkyl group being optionally substituted by one or more substituents selected from OH, halogen, —(C$_{1-3}$)alkoxy, wherein (alk) represents C$_{1-3}$alkylene and n represents 0 or 1.

(2) an aliphatic heterocyclic group of 4 to 6 membered rings containing at least one heteroatom selected from O, N or S, optionally substituted by one or more substituents selected from the group consisting of —(C$_{1-3}$)alkyl, —CO$_2$—(C$_{1-4}$)alkyl, —CO(C$_{1-3}$alkyl), —S(=O)$_n$—(C$_{1-3}$alkyl), —CONR$^a$R$^b$ (wherein R$^a$ and R$^b$ independently represent H or C$_{1-3}$alkyl) or =O; where there is a sulfur atom in the heterocycling ring, said sulfur is optionally substituted by (=O)$_n$, where n is 1 or 2.

(3) Straight or branched C$_{1-12}$ alkyl, optionally including one or more O, S(=O)$_n$ (where n is 0, 1 or 2) or N groups substituted within the alkyl chain, said alkyl optionally substituted by one or more of the following groups, phenyl, halogen, hydroxy or NR$^a$R$^b$ wherein R$^a$ and R$^b$ both represent C$_{1-3}$alkyl or hydrogen.

Z represents C$_{1-3}$-alkyl, halogen or hydrogen;

$Z^3$ represents a fluorinated straight or branched alkyl group of 1-6 carbon atoms (in the case of WO 99/24449) or said fluorinated alkyl group is attached to the furan fragment by an —OCH$_2$-linker (in the case of WO 99/24450);

Referring to the definitions of $Z^1$ to $Z^3$, it is further stated in WO 99/24449 and WO 99/24450 that:

Conveniently, $Z^1$ may represent (alk)$_n$—C$_{3-6}$-cycloalkyl wherein n is 0 or 1 and the said cycloalkyl is either substituted by at least one substituent selected from halogen, particularly fluorine, and OH, or is unsubstituted. Preferably n is zero. More preferably, the cycloalkyl group is mono-substituted with either OH or fluorine and more preferably the cycloalkyl ring has 5 carbon members.

Alternatively $Z^1$ may represent a substituted or unsubstituted aliphatic heterocyclic group, the substitutent being selected from the group consisting of —CO$_2$—C$_{1-4}$)alkyl, —CO—(C$_{1-3}$)alkyl, —S(=O)$_n$—(C$_{1-3}$)alkyl, CONR$^a$R$^b$ and when there is a heteroatom S in the ring this heteroatom may optionally be substituted by (=O)$_n$ where n is 1 or 2. More preferably the heterocyclic ring is unsubstituted or the substituents are —CO$_2$—(C$_4$)alkyl, or when the heteroatom is S, the substituent (=O)$_n$ is attached to the heterocyclic sulfur atom. More preferably in the case of WO 99/24450, when there is a sulfur heteroatom in the ring this S is unsubstituted.

Conveniently, the aliphatic heterocyclic groups is unsubstituted or when the substituent is —CO$_2$(C$_{1-4}$)alkyl, the heteroatom is N and the substituent is directly attached to said ring nitrogen atom.

Preferably the heterocyclic ring is 6 membered and more preferably contains only one O, N or S heteroatom.

Alternatively, $Z^1$ may represent a straight or branched alkyl of 1-6 carbon atoms (WO 99/24449) or 1-5 carbon atoms (WO 99/24450) optionally with at least one S(=O)$_n$ and/or N substituted in the chain, where there is an S(=O)$_n$ in the chain, preferably n is 1 or 2. The alkyl group conveniently may be unsubstituted or substituted by at least one OH group.

$Z^2$ preferably represents hydrogen, methyl or halogen, more preferably hydrogen, chlorine or Oust for WO 99/24450) methyl.

$Z^3$ preferably represents a $C_{1-3}$ fluoroalkyl group especially a fluoromethyl or (just for WO 99/24449) fluoroethyl group, more preferably $F_2C(Me)$—, $FCH_2$— (WO 99/24449) or $F_3C$— (WO 99/24450).

As examples, 5'deoxy-5'-fluoro-N-(2S-hydroxy-cyclopent-(S)-yl)-adenosine and 5'-deoxy-5'-fluoro-N-(2,2-dimethyl-propyl)-adenosine are provided by WO 99/24449 and N-(2-pyridin-4-yl-ethyl)-5'-O-trifluoromethyl-adenosine, N-(2S-fluoro-cyclopent-(S)-yl)-5'-O-trifluoromethyl-adenosine, N-tert-butyl-5'-O-trifluoromethyl-adenosine, N-(2S-hydroxy-cyclopent-(S)-yl)-5'-O-trifluoromethyl-adenosine, N-(rel-2,3-dihydroxy-propyl)-5'-O-trifluoromethyl-adenosine, N-cyclopentyl-5'-O-(2,2,2-trifluoro-ethyl) adenosine and N-(2R-hydroxy-cyclopent-(R)-yl)-5'-O-(2,2,2-trifluoro-ethyl)-adenosine by WO 99/24450.

Compounds explicitly disclosed by WO 99/24449 or WO 99/24450 are as such not an object of the present invention.

WO 95/07921 discloses adenosine derivates according to the general formula (II) wherein $Z^2$ is halogen, amino, perhalomethyl, cyano, $C_{1-6}$-alkoxy, $C_{1-6}$-alkylthio or $C_{1-6}$-alkylamino. These compounds can be used for treating central nervous system ailments.

WO 97/33591 discloses the use of adenosine derivatives according to the general formula (II) for treating disorders related to cytokines in humans including autoimmune disorders, inflammation, arthritis, type I or type II diabetes, multiple sclerosis, stroke, osteoporosis, septic shock or menstrual complications.

According to WO 97/33591, compounds of the general formula (II) are defined as follows:

$Z^1$ is selected from the groups consisting of

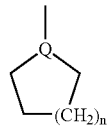
(a)

wherein Q is nitrogen or carbon, n is 1 to 3 and where the group (a) my be optionally substituted with one or two $C_{1-6}$-alkyl groups, $C_{2-6}$-alkenyl, $C_{2-6}$-alkynyl, phenoxy, phenylsulphonyl, phenylthio, hydroxy, phenyl, $C_{1-6}$-alkoxy or $C_{1-6}$-alkoxy, $C_{1-6}$-alkyl, phenylthioalkyl or

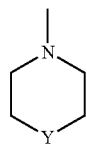
(b)

wherein Y is O, S or $NZ^4$, where $Z^4$ is H, $C_{1-6}$-alkyl or phenyl, and where the group (b) may be optionally substituted with $C_{1-6}$-alkyl, $C_{2-6}$-alkenyl, $C_{2-6}$-alkynyl, phenoxy, phenyl, $C_{1-6}$-alkoxy or $C_{1-6}$-alkoxy-$C_{1-6}$-alkyl, or $Z^1$ is —$NR^2R^3$ or —$YR^4$, wherein Y is oxygen;

$R^2$ is $C_{1-6}$-alkyl;

$R^3$ is phenyl or $C_{1-6}$-alkyl which may be substituted by phenyl or phenoxy;

$R^4$ is straight-chain $C_{1-6}$-alkyl, branched $C_{3-8}$-alkyl, $C_{2-8}$-alkenyl or $C_{3-8}$-cycloalkyl, which may be substituted by phenyl or phenoxy which in turn may be substituted with nitro, halogen or amine;

$Z^2$ represents hydrogen, halogen, amino, perhalomethyl, cyano, $C_{1-6}$-alkyl, $C_{1-6}$-alkoxy, $C_{1-6}$-alkylthio, $C_{1-6}$-alkylamino or phenyl;

$Z^3$ is hydroxymethyl, methyl, chloromethyl, bromomethyl, fluoromethyl, cyanomethyl, aminomethyl, vinyl, methylthiomethyl or methoxymethyl.

Preferably $Z^1$ is —$OR^4$, wherein $R^4$ is straight-chain $C_{1-6}$-alkyl, branched $C_{3-8}$-alkenyl or $C_{3-8}$-cycloalkyl, which may be substituted by phenyl or phenoxy which in turn may be substituted with nitro, halogen or amine.

Thus, compounds of the general formula (I) according to the present invention are not explicitly disclosed by WO 97/33591. Compounds explicitly disclosed by WO 97/33591 are as such not object of the present invention.

Aspects of the pathophysiology of insulin resistance and type 2 diabetes:

Insulin resistance, which is defined as a state of reduced responsiveness to normal circulating concentrations of insulin, is a characteristic trait of type 2 diabetes and contributes to abnormalities in muscle, fat tissue and liver. Insulin resistance preceds the onset of type 2 diabetes, which develops when additional defects exist at the level of the pancreatic beta-cell. As long as the peripheral insulin resistance can be compensated by increased insulin production glucose homeostasis is balanced. Even in the absence of type 2 diabetes, insulin resistance is a key feature of other human disease states. Impaired insulin action coupled with hyperinsulinemia leads to a variety of abnormalities, including elevated triglycerides, low levels of HDL (high density lipoproteins), enhanced secretion of VLDL (very low density lipoproteins), disorders of coagulation, increased vascular resistance, changes in steroid hormone levels, attenuation of peripheral blood flow and weight gain. Thus, insulin resistance is often associated with central obesity, hypertension, polycystic ovarian syndrome, dyslipidemia, and atherosclerosis (JCI 106, 163-164, 2000).

Insulin resistance is characterized in the adipose tissue by increased lipolysis, which results in increased levels of free fatty acids, which by themselves contribute to reduced glucose utilisation in the muscle, to increased flux of fatty acids to the liver, with subsequent increased VLDL production, and to impairment of insulin secretion from the beta-cell; in the liver by increased hepatic glucose production, and VLDL secretion, which result in hyperglycemia and hypertriglyceridemia, respectively; in the muscle by reduced glucose utilisation rates, which contribute to hyperglycemia.

Inhibition of peripheral lipolysis by adenosine A1 receptor agonists result in reduction of plasma free fatty acids (primary pharmacological effect). Reduced availability of free fatty acids to the muscle increases glucose utilisation and reduces VLDL production in the liver which is paralleld by reduced plasma triglycerides (secondary pharmacological effect).

Thus, there exists a strong need for compounds which can be employed for the treatment of insulin resistance and type 2 diabetes. The object of the present invention is to provide compounds showing this ability.

This object is attained by a class of metabolically stable adenosine analogues, and derivatives thereof, possessing unexpectedly desirable pharmacological properties, i.e. they are antilipolytic agents having a unique therapeutic profile, fat cell specific and devoid of direct cardio-chronotropic activity. Due to the compounds' specific activity on antilipolysis and the thereby obtained reduction of plasma lipids (e.g. free fatty acids and triglycerides), the compounds reduce both cardiovascular and metabolic risk factors and could also be useful for the treatment of cardiovascular diseases.

Therefore, this invention relates to adenosine analogues according to the general formula (I)

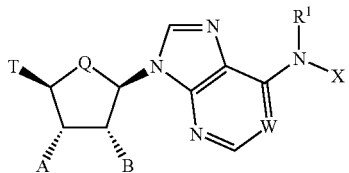

wherein:
W is N, N→O, or CH;
Q is $CH_2$ or O;
$R^1$ is selected from the group consisting of hydrogen, $C_1$-$C_{10}$-alkyl, allyl, 2-methylallyl, 2-butenyl and $C_1$-$C_{10}$-cycloalkyl;
X is selected from the group consisting of

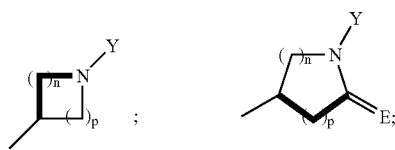

wherein n and p are independently 0, 1, 2, or 3, provided that n+p is at least 1;
and unsubstituted and at least monosubstituted $C_1$-$C_{10}$-alkylene-Y, $C_1$-$C_{10}$-alkenylene-Y, $C_3$-$C_{10}$-cycloalkylene-Y and $C_3$-$C_{10}$-cycloalkenylene-Y, the substituents of which are selected from the group consisting of halogens, pseudohalogens, $CF_3$, $C_1$-$C_6$-alkyl and $C_1$-$C_6$-alkoxy;
E is O or S;
Y is selected from the group consisting of hydrogen; and unsubstituted and at least monosubstituted $C_1$-$C_{10}$-alkyl, aryl, heterocyclyl, aryl-($C_1$-$C_{10}$-alkylene)- and heterocyclyl-($C_1$-$C_{10}$-alkylene), the substituents of which are selected from the group consisting of halogens, pseudohalogens, $C_1$-$C_6$-alkyl, $C_2$-$C_6$-alkenyl, $C_2$-$C_6$-alkynyl, aryl, heterocyclyl, $C_1$-$C_6$-alkoxy, $NH_2$, ($C_1$-$C_6$-alkyl)amino, di($C_1$-$C_6$-alkyl)amino, $C_1$-$C_6$-alkoxy-($C_1$-$C_6$-alkylene)-, nitro, carboxy, carbalkoxy, carboxy-($C_1$-$C_6$-alkylene)-, carbalkoxy-($C_1$-$C_6$-alkylene)-, hydroxy, hydroxy-($C_1$-$C_6$-alkylene)-, mercapto, ($C_1$-$C_6$-alkyl)thio, mercapto-($C_1$-$C_6$-alkylene)-, $C_1$-$C_6$-alkyl substituted by at least one halogen, ($C_1$-$C_6$-alkyl)sulfonyl-, aminosulfonyl-, ($C_1$-$C_6$-alkyl)aminosulfonyl-, ($C_1$-$C_6$-alkyl)sulfonylamido-, ($C_1$-$C_6$-alkyl) -sulfonyl-($C_1$-$C_6$-alkylene) amino-, $HO_3S$—($C_1$-$C_6$-alkylene)-, carbamoyl-($C_1$-$C_6$-alkylene)-, ($C_1$-$C_6$-alkyl)-carbamoyl, ($C_1$-$C_6$-alkyl)-C(O) O—, ($C_1$-$C_6$-alkyl)-CO—, —$SO_3H$ and carbamoyl;
T is a residue selected from the group consisting of $C_1$-$C_{10}$-alkyl, $C_1$-$C_{10}$-cycloalkyl, aryl-($C_1$-$C_{10}$-alkylene)- and heterocyclyl-($C_1$-$C_{10}$-alkylene), which residues are monosubstituted by halogen or $OR_2$, and which residues can be optionally substituted by at least one further substituent selected from the group consisting of halogens, pseudohalogens, mercapto, $NH_2$, nitro, hydroxy, unsubstituted and at least monosubstituted $C_1$-$C_6$-alkyl, $C_1$-$C_6$-alkoxy, ($C_1$-$C_6$-alkyl)amino, ($C_1$-$C_6$-alkyl)thio, aryl and heterocyclyl, the substituents of which are selected from the group consisting of halogens, pseudohalogens, $C_1$-$C_3$-alkyl, $C_1$-$C_3$-alkoxy and hydroxy;
$R^2$ is $C_1$-$C_{10}$-alkyl substituted by at least one halogen;
A is hydrogen, $C_1$-$C_{10}$-alkyl, hydroxy-($C_1$-$C_{10}$-alkylene)-, $C_1$-$C_{10}$-alkoxy-($C_1$-$C_{10}$-alkylene)-, or OR';
B ist hydrogen, $C_1$-$C_{10}$-alkyl, hydroxy-($C_1$-$C_{10}$-alkylene)-, $C_1$-$C_{10}$-alkoxy-($C_1$-$C_{10}$-alkylene)-, or OR";
R' and R" are independently selected from the group consisting of hydrogen, $C_1$-$C_6$-alkyl, aryl-($C_1$-$C_6$-alkylene)-, ($C_1$-$C_6$-alkyl)-CO, carbalkoxy, aryl-($C_1$-$C_6$-alkylene)-CO—, and aryl-O—CO—;

when A and B are OR' and OR", respectively, R' and R" together may form a substituent selected from the group consisting of

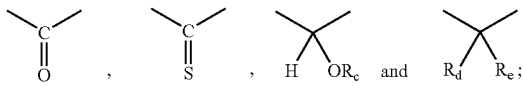

$R_C$ is hydrogen or $C_1$-$C_6$-alkyl;
$R_d$ and $R_e$ are independently hydrogen, $C_1$-$C_{10}$-alkyl, or together with the carbon atom to which they are attached may form a 1,1-cycloalkyl group;
heterocyclyl is a 4 to 10-membered, mono- or bicyclic heterocycle containing one or more heteroatoms selected from the group consisting of N, O and S;
aryl is phenyl, indan-1-yl, indan-2-yl, naphth-1-yl or naphth-2-yl;
or a pharmaceutically acceptable salt thereof, a pharmaceutically acceptable prodrug thereof, an N-oxide thereof, a hydrate thereof or a solvate thereof;
with the proviso that, in case Q is O and Y is hydrogen, X is not $C_3$-$C_6$-cycloalkylene or $C_3$-$C_6$-cycloalkylene substituted by at least one halogen; in case Q is O and Y is hydrogen, $C_1$-$C_{10}$-alkyl or $C_1$-$C_{10}$-alkyl substituted by at least one hydroxy, X is not unsubstituted $C_1$-$C_{10}$-alkylene; in case Q is O and Y—X is 2-pyridin-4-yl-ethyl, T is not $CF_3OCH_2$—; in case Q is O and T is methyl monosubstituted by halogen, Y—X is not unsubstituted and substituted $C_1$-$C_{10}$-alkyl, $C_1$-$C_{10}$-alkenyl, 2-phenylethyl or ($C_3$-$C_{10}$-cycloalkyl)methyl.

As used above and throughout the description of the invention, the following terms, unless indicated otherwise, shall be understood to have the following meanings:

If, in the compounds of formula (I), groups or substituents such as, for example, aryl, heteroaryl, alkyl etc., can be present several times, they all independently from each other have the meanings indicated and can hence, in each individual case, be identical with or different from each other. One example is the di($C_1$-$C_6$-alkyl)amino group in which the alkyl substitutents can be identical or different.

Alkyl, alkylene, alkenyl, alkenylene and alkynyl, residues can be linear or branched and are acyclic. This also applies when they are part of other groups, for example in alkoxy groups, alkoxycarbonyl groups or amino groups, or when they are substituted.

Examples for alkyl groups are methyl, ethyl, propyl, butyl, pentyl, hexyl, heptyl, octyl, nonyl, decyl, the n-isomers of these residues, isopropyl, isobutyl, isopentyl, sec-butyl, tert-butyl, neopentyl, 3,3-dimethylbutyl. Furthermore, unless stated otherwise, the term alkyl here also includes unsubstituted alkyl residues as well as alkyl residues which are substituted by one or more, for example one, two, three or four, identical or different residues, for example aryl groups. In substituted alkyl residues, for example arylalkyl, hydroxyalkyl such as —($C_1$-$C_3$)-alkyl-OH or alkoxyalkyl such as —($C_1$-$C_3$)-alkyl-O—($C_1$-$C_4$)-alkyl the substituents can be present in any desired position.

Examples for alkenyl and alkynyl groups are the vinyl residue, the 1-propenyl residue, the 2-propenyl residue (allyl residue), the 2-butenyl residue, the 2-methyl-2-propenyl residue, the 3-methyl-2-butenyl residue, the ethynyl residue, the 2-propynyl residue (propargyl residue), the 2-butynyl residue or the 3-butynyl residue.

Examples for alkylene groups are methylene, ethylene, propylene, butylene, pentylene, hexylene, heptylene, octylene, nonylene, decylene. Furthermore, unless stated otherwise, the term alkylene here also includes unsubstituted alkylene residues as well as alkylene residues which are substituted by one or more, for example one, two, three or four, identical or different residues, for example aryl groups, the substituents can be present in any desired position.

Examples for cycloalkyl residues containing at least three carbon atoms are cyclopropyl, cyclobutyl, cyclopentyl, cyclohexyl, cycloheptyl and cyclooctyl. All cycloalkyl groups can be substituted by one or more identical or different ($C_1$-$C_4$)-alkyl residues, in particular by methyl. Examples for substituted cycloalkyl residues are 4-methylcyclohexyl, 4-tert-butylcyclohexyl or 2,3-dimethylcyclopentyl.

Examples for cycloalkenyl residues are cyclopentenyl, cyclohexenyl, cycloheptenyl and cyclooctenyl. All cycloalkenyl groups can be substituted by one or more identical or different ($C_1$-$C_4$)-alkyl residues, in particular by methyl.

If not stated otherwise, the above-mentioned phenyl residues, naphthyl residues and indanyl residues can be unsubstituted or can carry one or more, for example one, two, three or four, of the substituents indicated in the above definition which can be in any desired position. If in compounds of the formula (I) nitro groups are present as substituents, in total only up to two nitro groups are preferably present in the molecule. In monosubstituted phenyl residues the substituent can be in the 2-position, the 3-position or the 4-position, in disubstituted phenyl residues the substituents can be in 2,3-position, 2,4-position, 2,5-position, 2,6-position, 3,4-position or 3,5-position. In trisubstituted phenyl residues the substituents can be in 2,3,4-position, 2,3,5-position, 2,3,6-position, 2,4,5-position, 2,4,6-position or 3,4,5-position. In fourfold substituted phenyl residues, the substituents can be in the 2,3,4,5-position, the 2,3,4,6-position, or the 2,3,5,6-position. Tolyl (=methylphenyl) can be 2-tolyl, 3-tolyl or 4-tolyl. Naphthyl can be 1-naphthyl or 2-naphthyl. In monosubstituted 1-naphthyl residues the substituent can be in the 2-position, the 3-position, the 4-position, the 5-position, the 6-position, the 7-position or the 8-position, in monosubstituted 2-naphthyl residues in the 1-position, the 3-position, the 4-position, the 5-position, the 6-position, the 7-position or the 8-position. In higher substituted naphthyl radicals, for example 1-naphthyl radicals or 2-naphthyl radicals which carry two or three substituents, the substituents can also be situated in all possible positions. Indanyl residues include indan-1-yl residues and indan-2-yl residues which can be unsubstituted or carry one or more of the substituents indicated. In case the indanyl residues are substituted, the substituent or substituents can be in any of the positions possible.

The above definitions as well as the following definitions relating to monovalent residues equally apply to the divalent residues phenylene, naphthylene and heteroarylene. Those divalent residues can be attached to the adjacent groups by any ring carbon atom. In the case of a phenylene residue, these can be in 1,2-position (ortho-phenylene), 1,3-position (meta-phenylene) or 1,4-position (para-phenylene). In the case of a naphthylene residue the free bonds can be in 1,2-position (=1,2-naphthylene or 1,2-naphthalinediyl) or in 1,3-position, 1,4-position, 1,5-position, 1,6-position, 1,7-position, 1,8-position, 2,3-position, 2,6-position or 2,7-position. In the case of 5-membered ring aromatics containing one heteroatom such as, for example, thiophene or furan, the two free bonds can be in 2,3-position, 2,4-position, 2,5-position or 3,4-position. A divalent residue derived from pyridine can be a 2,3-, 2,4-, 2,5-, 2,6-, 3,4- or 3,5-pyridinediyl residue. In the case of unsymmetrical divalent residues the present invention includes all positional isomers, i.e., in the case of a 2,3-pyridinediyl residue, for example, it includes the compound in which the one adjacent group is present in the 2-position and the other adjacent group is present in the 3-position as well as the compound in which the one adjacent group is present in the 3-position and the other adjacent group is present in the 2-position.

Unless stated otherwise, heterocyclyl residues including heteroaryl residues, heteroarylene residues and rings which are formed by two groups bonded to a nitrogen are preferably derived from heterocycles which contain one, two, three or four heteroatoms which can be identical or different; more preferably they are derived from heterocycles which contain one, two, or three, in particular one or two, heteroatoms which can be identical or different. Unless stated otherwise, the heterocycles can be monocyclic or polycyclic, for example monocyclic, bicyclic or tricyclic. Preferably they are monocyclic or bicyclic. The rings preferably are 5-membered rings, 6-membered rings or 7-membered rings. Examples of monocyclic and bicyclic heterocyclic systems from which residues occuring in the compounds of the formula (I) can be derived, are pyrrole, furan, thiophene, imidazole, pyrazole, 1,2,3-triazole, 1,2,4-triazole, 1,3-dioxole, 1,3-oxazole (=oxazole), 1,2-oxazole (=isoxazole), 1,3-thiazole (=thiazole), 1,2-thiazole (=isothiazole), tetrazole, pyridine, pyridazine, pyrimidine, pyrazine, pyran, thiopyran, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3-oxazepine, 1,3-thiazepine, indole, benzothiophene, benzofuran, benzothiazole, benzimidazole, benzodioxol, quinoline, isoquinoline, cinnoline, quinazoline, quinoxaline, phthalazine, thienothiophenes, morpholinyl, 1,8-naphthyridine and other naphthyridines, pteridin, or phenothiazine, each of them in saturated form (perhydro form) such as piperidine, pyrrolidine, tetrahydrofuran or tetrahydropyran or in partially unsaturated form (for example in the dihydro form or the tetrahydro form) or in maximally unsaturated form, in case the respective forms are known and stable. The term "aryl" and the term "heteroaryl" as used herein comprise bicyclic residues in which both cycles are aromatic as well as bicyclic residues in which only one cycle is aromatic. Suitable heterocycles include, for example, the saturated heterocycles pyrrolidine, piperidine, piperazine, morpholine and thiomorpholine. The degree of saturation of heterocyclic groups is indicated in their individual definitions. Unsaturated heterocycles can contain, for example, one, two or three double bonds within the ring system. 5-membered rings and 6-membered rings can in particular also be aromatic.

Substituents which may be derived from these heterocycles can be attached via any suitable carbon atom. Residues derived from nitrogen heterocycles can carry a hydrogen atom or a substituent on a ring nitrogen atom, and examples include pyrrole, imidazole, pyrrolidine, morpholine, piperazine residues, etc. Those nitrogen heterocyclic residues can also be attached via a ring nitrogen atom, in particular if the respective heterocyclic residue is bonded to a carbon atom. For example, a thienyl residue can be present as 2-thienyl residue or 3-thienyl residue, a furyl residue as 2-furyl residue or 3-furyl residue, a pyridyl residue as 2-pyridyl residue, 3-pyridyl residue or 4-pyridyl residue, a piperidinyl residue as 1-piperidinyl residue (=piperidino residue), 2-piperidinyl residue, 3-piperidinyl residue or 4-piperidinyl residue, a (thio)morpholinyl residue as 2-(thio)morpholinyl residue, 3-(thio)morpholinyl residue or 4-(thio)morpholinyl residue (=thiomorpholino residue). A residue derived from 1,3-thiazole or imidazole which is attached via a carbon atom can be attached via the 2-position, the 4-position or the 5-position.

In case a heterocyclic groups is substituted, it can carry one or more, for example one, two, three or four, identical or different substituents. Substituents in heterocycles can be present in any desired positions, for example in a 2-thienyl residue or 2-furyl residue in the 3-position and/or in the 4-position and/or in the 5-position, in a 3-thienyl residue or 3-furyl residue in the 2-position and/or in the 4-position and/or in the 5-position, in a 2-pyridyl residue in the 3-position and/or in the 4-position and/or in the 5-position and/or in the 6-position, in a 3-pyridyl residue in the 2-position and/or in the 4-position and/or in the 5-position and/or in the 6-position, in a 4-pyridyl residue in the 2-position and/or in the 3-position and/or in the 5-position and/or in the 6-position. Suitable nitrogen heterocycles can also be present as N-oxides or as quarternary salts containing a counterion which is derived from a pharmaceutically acceptable acid. Pyridyl residues, for example, can be present as pyridine-N-oxides.

Halogen is fluorine, chlorine, bromine oder iodine, preferably fluorine or chlorine.

Examples for pseudohalogens are CN and $N_3$, a preferred pseudohalogen is CN.

"Alkoxy" means an alkyl-O group in which "alkyl" is as previously described. Exemplary groups include methoxy, ethoxy, n-propoxy, i-propoxy and n-butoxy. "Carbalkoxy" means a carboxyl substituent esterified with an alcohol of the formula $C_nH_{2n+1}OH$, wherein n is from 1 to about 6.

"Prodrug" means a compound which is rapidly transformed in vivo to yield a compound according to formula (I), for example by hydrolysis in blood. "Pharmaceutically acceptable prodrug" means a compound which is, within the scope of sound medical judgement, suitable for pharmaceutical use in a patient without undue toxicity, irritation, allergic response, and the like, and effective for the intended use, including a pharmaceutically acceptable ester as well as a zwitterionic form, where possible, of the peptide compounds of the invention. Pharmaceutically acceptable prodrugs according to the invention are described in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include ethanolates, methanolates, and the like. "Hydrate" is a solvate wherein the solvent molecule(s) is/are $H_2O$.

The compounds of Formula I contain chiral (asymmetric) centers. The invention includes the individual stereoisomers in the form of enantiomers and diastereoisomers and mixtures of the stereoisomers. The individual isomers are prepared or isolated by methods well known in the art or by methods described herein after.

The compounds described herein may be used in the form of the free base, in the form of acid addition salts or as hydrates. All such forms are within the scope of the invention. Acid addition salts are simply a more convenient form for use. In practice, use of the salt form inherently amounts to use of the base form. The acids which may be used to prepare the acid addition salts include preferably those which produce, when combined with the free base, pharmaceutically acceptable salts, that is, salts whose anions are non-toxic to the recipient in pharmaceutical doses of the salts, so that the beneficial antilipolytic effects produced by the free base are not vitiated by side effects ascribable to the anions. Although pharmaceutically acceptable salts of the compounds of the invention are preferred, all acid addition salts are useful as sources of the free base form, even if the particular salt, per se, is desired only as an intermediate product as, for example, when the salt is formed only for purposes of purification and identification, or when it is used as an intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid, and sulfamic acid; and organic acids such as acetic acid, citric acid, lactic acid, tartaric acid, malonic acid, methanesulfonic acid, fumaric acid, ethanesulfonic acid, benzenesulfonic acid, p-toluenesulfonic acid, cyclohexylsulfamic acid, quinic acid and the like. The corresponding acid addition salts comprise the following: hydrochloride, sulfate, phosphate, sulfamate, acetate, citrate, lactate, tartarate, methanesulfonate, fumarate, ethanesulfonate, benzenesulfonate, p-toluenesulfonate, cyclohexylsulfonate and quinate, respectively.

The acid addition salts of the compounds of the invention are conveniently prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Included within the scope of formula I are classes of compounds which may be characterized generally as N6-substituted adenosines; N6-substituted carbocyclic adenosines (or, alternatively, dihydroxy[N6-substituted-9-adenyl]cyclopentanes) and N-oxides thereof. Also within the scope of formula I are the derivatives of compounds of the above classes in which one or both of the 2- or 3-hydroxyl groups of the cyclopentane ring or, in the cases of classes of compounds containing the ribose moiety, the 2'- or 3'-hydroxyl groups of the ribose ring are substituted. Such derivatives may themselves comprise the biologically active chemical entity useful in the treatment of insulin resistance and as antilipolytic agents, or may act as pro-drugs to such biologically active compounds which are formed therefrom under physiological conditions.

Preferred compounds of the formula (I) are those compounds in which one or more of the residues contained therein have the meanings given below, with all combinations of preferred substituent definitions being a subject of the present invention. With respect to all preferred compounds of the formula (I) the present invention also includes all pharmaceutically acceptable salts thereof, pharmaceutically acceptable prodrugs thereof, N-oxides thereof, hydrates thereof or solvates thereof.

In preferred embodiments of the present invention, the substituents $R^1$, A, B, Q, T, W, X and Y of the formula (I) indepently from each other have the following meanings.

Hence, one or more of the substituents $R^1$, A, B, Q, T, W, X and Y can have the preferred meaning(s), the more preferred meaning(s), the even more preferred meaning(s), the much more preferred meaning(s) and/or the most preferred meaning(s) given below.

W is preferably N;

Q is preferably $CH_2$;

$R^1$ is preferably hydrogen or $C_1$-$C_6$-alkyl; $R^1$ is most preferably hydrogen;

X is preferably selected from the group consisting of

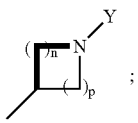

and unsubstituted and at least monosubstituted $C_1$-$C_{10}$-alkylene-Y and $C_3$-$C_{10}$-cycloalkylene-Y, the substituents of which are selected from the group consisting of halogens, pseudohalogens, $CF_3$, $C_1$-$C_6$-alkyl and $C_1$-$C_6$-alkoxy;

X is more preferably selected from the group consisting of

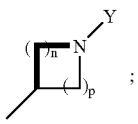

and unsubstituted and at least monosubstituted $C_1$-$C_6$-alkylene-Y, the substituents of which are selected from the group consisting of $CH_3$, $CH_3$—$CH_2$, Cl, F, $CF_3$ and $CH_3$—O;

n+p is preferably 3 or 4;

Y is preferably selected from the group consisting of hydrogen; and unsubstituted and at least monosubstituted $C_1$-$C_{10}$-alkyl, aryl and heterocyclyl, the substituents of which are selected from the group consisting of halogens, pseudohalogens, $C_1$-$C_6$-alkyl, $C_1$-$C_6$-alkoxy, $NH_2$, ($C_1$-$C_6$-alkyl)amino, di($C_1$-$C_6$-alkyl)amino, $C_1$-$C_6$-alkoxy-($C_1$-$C_6$-alkylene)-, nitro, carboxy, carbalkoxy, hydroxy, hydroxy-($C_1$-$C_6$-alkylene)-, mercapto, ($C_1$-$C_6$-alkyl)thio, mercapto-($C_1$-$C_6$-alkylene)-, $C_1$-$C_6$-alkyl substituted by at least one halogen, ($C_1$-$C_6$-alkyl)sulfonyl-, aminosulfonyl-; ($C_1$-$C_6$-alkyl)aminosulfonyl-, ($C_1$-$C_6$-alkyl)sulfonylamido-, $SO_3H$ and carbamoyl;

Y is more preferably selected from the group consisting of unsubstituted and at least monosubstituted aryl and heterocyclyl, the substituents of which are selected from the group consisting of halogens, pseudohalogens, $C_1$-$C_3$-alkyl, $C_1$-$C_3$-alkoxy, $NH_2$, ($C_1$-$C_3$-alkyl)amino, di($C_1$-$C_3$-alkyl)amino, $C_1$-$C_3$-alkoxy-($C_1$-$C_3$-alkylene)-, nitro, carboxy, hydroxy, hydroxy-($C_1$-$C_3$-alkylene)-, mercapto, ($C_1$-$C_3$-alkyl)thio, mercapto-($C_1$-$C_3$-alkylene)-, and $CF_3$;

Y is most preferably selected from the group consisting of unsubstituted and at least monosubstituted phenyl, pyridyl and thienyl, the substituents of which are selected from the group consisting of halogens, $C_1$-$C_3$-alkyl, $C_1$-$C_3$-alkoxy, hydroxy, mercapto and $CF_3$;

T is preferably $C_1$-$C_{10}$-alkyl which is monosubstituted by halogen or $OR^2$, and which $C_1$-$C_{10}$-alkyl can furthermore be optionally substituted by at least one substituent selected from the group consisting of halogens, pseudohalogens, mercapto, $NH_2$, nitro, hydroxy, unsubstituted and at least monosubstituted $C_1$-$C_6$-alkyl, $C_1$-$C_6$-alkoxy, ($C_1$-$C_6$-alkyl)amino, ($C_1$-$C_6$-alkyl)thio, aryl and heterocyclyl, the substituents of which are selected from the group consisting of halogens, pseudohalogens, $C_1$-$C_3$-alkyl, $C_1$-$C_3$-alkoxy and hydroxy;

T is more preferably $C_1$-$C_{10}$-alkyl substituted by at least one substituent selected from the group consisting of halogen and $OR^2$;

T is even more preferably $C_1$-$C_6$-alkyl substituted by at least one substituent selected from the group consisting of fluorine and $OR^2$;

T is much more preferably fluoromethyl, trifluoromethoxymethyl or difluoromethoxymethyl; T is most preferably fluoromethyl;

$R^2$ is preferably $C_1$-$C_{10}$-alkyl substituted by at least one fluorine;

$R^2$ is more preferably $C_1$-$C_3$-alkyl substituted by at least one fluorine;

$R^2$ is most preferably $CF_3$;

A is preferably OR';

B is preferably OR";

Preferably, R' and R" are both hydrogen, or R' and R" preferably together form a substituent selected from the group consisting of

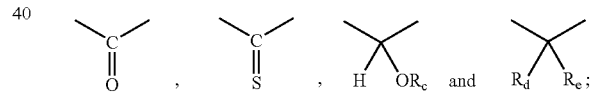

R' and R" more preferably together form

$R_c$ is preferably hydrogen or methyl;

$R_d$ and $R_e$ are preferably independently hydrogen, or $C_1$-$C_6$-alkyl; $R_d$ and $R_e$ are more preferably both $C_1$-$C_3$-alkyl; $R_d$ and $R_e$ are even more preferably both methyl;

A and B are most preferably both hydroxy;

heterocyclyl is preferably selected from the group consisting of pyridyl, pyridazinyl, pyrimidinyl, isoquinolinyl, quinolinyl, quinazolinyl, imidazolyl, pyrrolyl, furanyl, thienyl, thiazolyl, benzothiazolyl, piperidinyl, pyrrolidinyl, tetrahydrofuranyl, tetrahydropyranyl, and morpholinyl;

heterocyclyl is more preferably selected from the group consisting of pyridyl, pyridazinyl, pyrimidinyl, imidazolyl, thienyl, thiazolyl, benzothiazolyl, piperidinyl, pyrrolidinyl, tetrahydrofuranyl, and morpholinyl;

heterocycyl is most preferably pyridyl or thienyl;

aryl is preferably phenyl, naphta-1-yl or naphtha-2-yl; aryl is most preferably phenyl.

Compounds of the formula (I) in which some or all of the above-mentioned groups have the preferred meanings, the more preferred meanings the even more preferred meanings, the much more preferred meanings or the most preferred meanings defined above are also an object of the present invention.

Most preferred compounds according to the general formula (I) are selected from the groups consisting of (1R,2S,3R,5S)-3-{6-[1-(3-chloro-phenyl-1-yl)-pyrrolidin-3(S)-ylamino]-purin-9-yl}-5-fluoromethyl-cyclopentane-1,2-diol, (1R,2S,3R,5S)-3-{6-[(R)-1-(3-chloro-thiophen-2-yl-methyl)-propylamino]-purin-9-yl}-5-fluoromethyl-cyclopentane-1,2-diol and (1R,2S,3R,5R)-3-{6-[1-(3-chloro-phenyl-1-yl)-pyrrolidin-3(S)-ylamino]-purin-9-yl}-5-trifluoromethoxymethyl-cyclopentane-1,2-diol;

or a pharmaceutically acceptable salt thereof, a pharmaceutically acceptable prodrug thereof, an N-oxide thereof, a hydrate thereof or a solvate thereof.

Compounds of this invention may be prepared by known methods or in accordance with the reaction sequences described below. The starting materials used in the preparation of compounds of the invention are known or commercially available, or can be prepared by known methods or by specific reaction schemes described herein.

The present invention also relates compounds according to the general formula (I) pharmaceutically acceptable salts thereof, pharmaceutically acceptable prodrugs thereof, N-oxides thereof, hydrates thereof or solvates thereof, with the definitions of $R^1$, A, B, Q, T, W and Y given above, for use as pharmaceuticals.

Pharmaceuticals containing compounds of the formula (I), in which one or more, including all, of the above-mentioned groups have the preferred meanings, the more preferred meanings, the even more preferred meanings, the much more preferred meanings and/or the most preferred meanings defined above are also an object of the present invention.

The compounds according to the formula (I) can be used for the treatment of insulin resistance or for providing an anti-lipolytic effect. In the context of the present invention treatment includes the therapy as well as the prophylaxis of the respective deseases.

Examples of diseases which can be treated with the compounds according to the present invention include type 2 diabetes, metabolic syndrome, insulin resistance, lipid disorders such as hyper-triglyceridinia or cardiovascular disease. Preferably, compounds of the formula (I) can be employed for the treatment of type 2 diabetes or insulin resistance.

The compounds of the formula (I) and their pharmaceutically acceptable salts, optionally in combination with other pharmaceutically active compounds, can be administered to animals, preferably to mammals, and in particular to humans, as pharmaceuticals by themselves, in mixtures with one another or in the form of pharmaceutical preparations. Further subjects of the present invention therefore also are the compounds of the formula (I) and their pharmaceutically acceptable salts for use as pharmaceuticals, and in particular their use in the therapy and prophylaxis of the above-mentioned diseases and syndromes as well as their use for preparing medicaments for these purposes. Furthermore, subjects of the present invention are pharmaceutical preparations (or pharmaceutical compositions) which comprise an effective dose of at least one compound of the formula (I) and/or pharmaceutically acceptable salt thereof and a pharmaceutically acceptable carrier, i.e. one or more pharmaceutically acceptable carrier substances and/or additives.

The amount of a compound of formula (I) which is necessary to achieve the desired biological effect depends on a number of factors, for example the specific compound chosen, the intended use, the mode of administration and the clinical condition of the patient. In general, the daily dose is in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can most suitably be administered as infusion of from 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. It is thus possible for ampoules for injections to contain, for example, from 1 mg to 100 mg, and single-dose formulations which can be administered orally, such as, for example, tablets or capsules, to contain, for example, from 1.0 to 1000 mg, typically from 10 to 600 mg. In the case of pharmaceutically acceptable salts, the aforementioned weight data are based on the weight of the salt of the compound of formula (I).

For the prophylaxis or therapy of the above-mentioned conditions, the compounds of formula (I) can be used as the compound itself, but they are preferably in the form of a pharmaceutical composition with an acceptable carrier. The carrier must, of course, be acceptable in the sense that it is compatible with the other ingredients of the composition and is not hazardous for the patient's health. The carrier may be a solid or a liquid or both and is preferably formulated with the compound as single dose, for example as tablet which may contain from 0.05% to 95% by weight of the active ingredient.

Within the present invention, the term combination preparation means the combination of at least one compound according to the general formula (I) with at least one further pharmaceutically active substance. Such combination preparations are also an subject of the present invention. Pharmaceutically active substances which can be used for combination preparations according to the present invention are as follows:

All antidiabetics mentioned within the Rote Liste 2002, Kapitel (chapter) 12 [Antidiabetika (antidiabetics)] (Rote Liste 2002, Arzneimittelverzeichnis für Deutschland (einschließlich EU-Zulassungen und bestimmter Medizinprodukte); editor: Rote Liste® Service GmbH, Frankfurt/Main, Germany; ECV Editio Cantor Verlag, Aulendorf, Germany; ISBN 3-87193-252-3), such antidiabetics can, in particular, be combined with compounds according to the general formula (I) for the synergetic improvement of efficacy. The administration of pharmaceutically active substances in combination with compounds according to the general formula (I) can be done either individually or in form of combination preparations. Most of the below described pharmaceutically active substances are described in USP Dictionary of USAN and International Drug Names, US Pharmacopeia Rockville 2001.

Antidiabetics comprise insulin, derivatives of insulin such as Lantus® or HMR 1964, quickly effective insulins according to U.S. Pat. No. 6,221,663, GLP-1-derivatives such as those described in WO 98/08871 (Novo Nordisk A/S) and orally effective hypoglycemic drugs.

The orally effective hypoglycemic drugs preferably comprise sulfonylurea, biguanidines, meglitinides, oxadiazolidindions, thiazolidindions, glucosidase inhibitors, glucagone antagonists, GLP-1-agonists, and potassium channel openers such as those described, for example, in WO 97/26265 or WO 99/03861 (Novo Nordisk A/S), insulin sensitizers, inhibitors of liver enzymes participating at the stimulation of gluconeogenesis and/or glycogenolysis, modulators of the uptake of glucose, such as inhibitors of enteral glucose resroption (e.g. inhibitors of the sodium dependent glucose transporter 1 (SGLT-1), inhibitors of the renal re-absorption of glucose (e.g. inhibitors of the sodium dependent glucose transporter 2 (SGLT-2)), inhibitors of the hepatic glucose output (e.g. inhibitors of the glycogen phosphorylase), compounds changing the lipometabolism such as antihyperlipidemic compounds and antilipidemic compounds, compounds reducing the food intake (all slimming agents/anorexics mentioned within the "Rote Liste 2002, Kapitel (chapter) 01 [Abmagerungsmittel/Appetitzügler//slimming agents/anorexics] (Rote Liste 2002, Arzneimittelverzeichnis für Deutschland (einschließlich EU-Zulassungen und bestimmter Medizinprodukte); editor: Rote Liste® Service GmbH, Frankfurt/Main, Germany; ECV Editio Cantor Verlag, Aulendorf, Germany; ISBN 3-87193-252-3))", compounds modulating the energy output (e.g. β3agonists), PPAR- and PXR-agonists and compounds which are effective on the ATP depending potassium channel of beta cells.

In one embodiment of the present invention compounds according to general formula (I) are administered in combination with an HMGCoA reductase inhibitor such as simvastatine, fluvastatine, pravastatine, lovastine, atorvastatine, cerivastatine or rosuvastatine.

In another embodiment of the present invention compounds according to a general formula (I) are advantages in combination with an inhibitor of cholesterol resorption such as ezetimibes, tiquesides or pamaquesides.

In another embodiment of the present invention compounds according to the general formula (I) are administered in combination with a PPAR gamma agonist such as rosiglitazon, pioglitazon, JTT-501 or GI 262570.

In another embodiment of the present invention compounds according to the general formula (I) are administered in combination with PPAR alpha agonists, such as GW 9578 or GW 7674.

In another embodiment of the present invention compounds according to general formula (I) are administered in combination with mixed PPAR alpha/gamma agonists such as GW 1536, AVE 8042, AVE 8134, AVE 0847, or as described in WO 00/11833, W 00/11490 and DE 101 42 734.4.

In another embodiment of the present invention compounds according to general formula (I) are administered in combination with a fibrate, such as fenofibrate, clofibrate or bezafibrate.

In another embodiment of the present invention compounds according to the general formula (I) are administered in combination with an MTP inhibitor such as implitapide, BMS-201038 or R-103757.

In another embodiment of the present invention compounds according to the general formula (I) are administered in combination with an inhibitor of colic acid resorption according to the U.S. Pat. No. 6,245,744 or U.S. Pat. No. 6,221,897 such as HMR 1741.

In another embodiment of the present invention compounds according to the general formula (I) are administered in combination with a CETP inhibitor, such as JTT-705.

In another embodiment of the present invention, compounds according to the general formula (I) are administered in combination with a polymeric absorber of colic acid, such as cholestyramine or colesevelam.

In another embodiment of the present invention compounds according to the general formula (I) are administered in combination with a LDL-receptor inducer according to U.S. Pat. No. 6,342,512, such as HMR1171 or HMR 1586.

In another embodiment of the present invention, compounds according to a general formula (I) are administered in combination with an ACAT inhibitor, such as avasimibe.

In another embodiment of the present invention compounds according to a general formula (I) are administered in combination with an antioxidant such as OPC-14117.

In another embodiment of the present invention, compounds according to the general formula (I) are administered in combination with the lipoprotein lipase inhibitor, such as NO-1886.

In another embodiment of the present invention, compounds according the general formula (I) are administered in combination with a ATP-citrate lyase-inhibitor, such as SB-204990.

In another embodiment of the present invention, compounds according to the general formula (I) are administered in combination with a squalene synthetase inhibitor, such as BMS-188494.

In another embodiment of the present invention, compounds according to the general formula (I) are administered in combination with the lipoprotein antagonist, such as CI-1027 or nicotinic acid.

In another embodiment of the present invention, compounds according to the general formula (I) are administered in combination with the lipase inhibitor, such as orlistate.

In another embodiment of the present invention, compounds according to the general formula (I) are administered in combination with insulin.

In another embodiment of the present invention, compounds according to the general formula (I) are administered in combination with a sulphonylurea, such as tolbutamide, glibenclamide, glipicide or glimepiride.

In another embodiment of the present invention, compounds accoriding to the general formula (I) are administered in combination with a biguanide, such as metoformine.

In another embodiment of the present invention, compounds according to the general formula (I) are administered in combination with a meglitinide, such as repaglinide.

In another embodiment of the present invention, compounds according to the general formula (I) are administered in combination with a thiazolidindion, such as troglitazon, ciglitazon, pioglitazon, rosigliatazon or compounds according to WO 97/41097 (Dr. Reddy's Research Foundation) in particular 6-[[4-[(3,5-dihydro-3-methyl-4-oxo-2-chinazolinyl-methoxy]phenyl]methyl]-2,4-thiazolidindione.

In another embodiment of the present invention, compounds according to the general formula (I) are administered in combination with an α-glucosidase inhibitor, such as miglitol or acarbose.

In another embodiment of the present invention, compounds according to the general formula (I) are administered in combination with a drug which is effective on the ATP depending potassium channel of beta cells, such as tolbutamide, glibenclamide, glipizide, glimepiride or repaglinide.

In another embodiment of the present invention, compounds according to the general formula (I) are administered in combination with more one of the above mentioned pharmaceutically active compounds, e.g. in combination with a sulphonylurea and metformin, a sulphonylurea and acarbose, repaglinid and metformin, insulin and a sulphonylurea, insulin and metformin, insulin and troglitazon, insulin and lovastatin.

In another embodiment of the present invention, compounds according to the general formula (I) are administered in combination with CART-modulatores (according to "cocaine-amphetamine-regulated-transcript influences energy metabolism, anxiety and gastric emptying in mice" Asakawa, A, et al., M.: Hormone and Metabolic Research (2001), 33(9), 554-558), NPY-antagonists such as naphthalin-1-sulfonic acid {4-[(4-amino-quinazolin-2-ylamino)-methyl]-cyclohexylmethyl}-amide; (hydrochlorid (CGP 71683-A)) MC4-agonists such as 1-amino-1,2,3,4-tetrahydro-naphthalin-2-carboxylic acid [2-(3a-benzyl-2-methyl-3-oxo-2,3,3a,4,6,7-hexahydro-pyrazolo[4,3-c]pyridin-5-yl)-1-(4-chloro-phenyl)-2-oxo-ethyl]-amide; (WO 01/91752)), orexin antagonists, such as 1-(2-methyl-benzoxazol-6-yl)-3-[1,5]naphthyridin-4-yl-urea; (hydrochloride (SB-334867-A)), H3 agonists such as 3-cyclohexyl-1-(4,4-dimethyl-1,4,6,7-tetrahydro-imidazo[4,5-c]pyridin-5-yl)-propan-1-on, oxalic acid salt (WO 00/63208)), TNF agonists, CRF antagonists, such as [2-methyl-9-(2,4,6-trimethyl-phenyl)-9H-1,3,9-triaza-fluoren-4-yl]-dipropyl-amine (WO 00/66585), CRF BP antagonists such as urocortin, urocortin agonists, beta 3-agonists such as 1-(4-chloro-3-methanesulfonylmethyl-phenyl)-2-[[2-(2,3-dimethyl-1-H-indol-6-yloxy)-ethylamino]-ethanol; hydrochloride (WO 01/83451), MSH (melanocyt stimulating hormone) agonists, CCK-A agonists such as {2-[4-(4-Chloro-2,5-dimethoxyphenyl)-5-(2-cyclohexyl-ethyl)-thiazol-2-ylcarbamoyl]-5,7-dimethyl-indol-1-yl}-acetic acid trifluoroacetic acid salt (WO 99/15525), serotonin-reabsorption inhibitors, such as dexfenfluramines, mixed sertonin and noradrenergic compounds according to WO 00/71549, 5HT-agonists such as 1-(3-ethyl-benzofuran-7-yl)-piperazine oxalic acid salt (WO 01/09111), bombesine agonists, galanine antagonists, growth hormone such as human growth hormone, compounds releasing growth hormone such as 6-benzyloxy-1-(2-diisopropylamino-ethylcarbamoyl)-3,4,dihydro-1H-isoquinoline-2-carboxylic acid tert-butyl ester (WO 01/85695), TRH agonists according to EP 0 462 844, uncoupling protein 2 or 3 modulators, leptinagonists according to Lee, Daniel W.; Leinung, Mattew C.; Rozhavskaya-Arena, Marina; Grasso, Patricia; Leptin agonists as a potential approach to the treatment of obesity; Drugs of the Future (2001), 26 (9), 873-881, DA agonists such as bromocriptin or doprexin, lipase/amylase inhibitors according to WO 00/40569, PPAR modulators according to WO 00/78312, RXR modulators or TR agonists.

In another embodiment of the present invention compounds according to the general formula (I) are administered with the pharmaceutically active compound leptin according to e.g. "perspectives in the therapeutic use of leptin", Salvador, Javier; Gomez-Ambrosi, Javier; Fruhbeck, Gema, Expert Opinion on Pharmacotherapy (2001, 2 (10), 1615-1622.

In another embodiment of the present invention compounds according to the general formula (I) are administered in combination with the pharmaceutically active substances dexamphatamine or amphetamine.

An another embodiment of the present invention, compounds according to the general formula (I) are administered in combination with the pharmaceutically acitve substances fenfluramine or dexfenfluramine.

In another embodiment of the present invention, compounds according to the general formula (I) are administered in combination with the pharamaceutically active compound sibutramine.

In another embodiment of the present invention, compounds according to the general formula (I) are administered in combination with the pharmaceutically acitve substance orlistate.

In another embodiment of the present invention the compounds according to the general formula (I) are administered in combination with the pharmaceutically acitve substances mazindol or phentermin.

In another embodiment of the present invention, compounds according to the general formula (I) are administered in combination with bulk material, preferably insoluble bulk material (according to, e.g., Carob/Caromax® (Zunft H J; et al., Carob pulp preparation for treatment of hypercholesterolemia, ADVANCES IN THERAPY (2001 September-October), 18(5), 230-6) Caromax is a product containing carob of the company Nutrinova, Nutrition Specialties& Food Ingredients GmbH, Industriepark Höchst, 65926 Frankfurt/Main, Germany). Compounds according to the general formula I and Caromax® can be administered either as a combination preparation or individually. Caromax® can also be adminsterated as nutritions, such as within bicuits or muesli bars.

In another embodiment of the present invention, compounds according to the general formula (I) are administered in combination with at least one compound selected from the groups consisting of statins; ACE-inhibitors; AT1-antagonists; Ca-antagonists; beta-blockers; vitamins, in particular vitamin C and vitamin B6 and niacine.

Subject of the present invention are also combination preparations containing at least on compound according to a general formula (I), at least one of the pharmaceutically active substances as indicated above and additional pharmaceutically acitve substances which are not indicated above.

The pharmaceutical compositions according to the invention can be produced by one of the known pharmaceutical methods which essentially consist of mixing the ingredients with pharmacologically acceptable carriers and/or excipients.

Besides compounds according to the invention and carriers, the pharmaceutical preparations can also contain additives, for example fillers, disintegrants, binders, lubricants, wetting agents, stabilizers, emulsifiers, dispersants, preservatives, sweeteners, colorants, flovorings, aromatizers, thickeners, diluents, buffer substances, solvents, solubilizers, agents for achieving a depot effect, salts for altering the osmotic pressure, coating agents or antioxidants.

Pharmaceutical compositions according to the invention are those suitable for oral, rectal, topical, peroral (for example sublingual) and parenteral (for example subcutaneous, intramuscular, intradermal or intravenous) administration although the most suitable mode of administration in each individual case depends on the nature and severity of the condition to be treated and on the nature of the compound of formula (I) used in each case.

Coated formulations and coated slow-release formulations also lie within the scope of the invention. Formulations resistant to acid and gastric fluid are preferred. Suitable coatings resistant to gastric fluid comprise cellulose acetate phthalate, polyvinyl acetate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula (I); as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. In general, the compositions are produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tabletting the compound in free-flowing form, such as, for example, a powder or granules, where appropriate mixed with a binder, lubricant, inert diluent and/or a (plurality of) surface-active/dispersing agent(s) in a suitable machine. Molded tablets can be produced by molding the compound which is in powder form and is moistened with an inert liquid diluent in a suitable machine.

Pharmaceutical compositions suitable for peroral (sublingual) administration comprise suckable tablets which contain a compound of formula (I) with a flavoring, normally sucrose and gum arabic or tragacanth, and pastilles which comprise the compound in an inert base such as gelatin and glycerol or sucrose and gum arabric.

Suitable pharmaceutical compositions for parenteral administration comprise preferably sterile aqueous preparations of a compound of formula (I), which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions according to the invention generally contain from 0.1 to 5% by weight of the active compound.

Suitable pharmaceutical compositions for rectal administration are preferably in the form of single-dose suppositories. These can be produced by mixing a compound of formula (I) with one or more conventional solid carriers, for example cocoa butter, and shaping the resulting mixture.

Suitable pharmaceutical compositions for topical application to the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Suitable pharmaceutical compositions for transdermal uses can be in the form of single plasters which are suitable for long-term close contact with the patient's epidermis. Such plasters suitably contain the active ingredient in an optionally buffered aqueous solution, dissolved and/or dispersed in an adhesive or dispersed in a polymer. A suitable active ingredient concentration is about 1% to 35%, preferably about 3% to 15%. As a special possibility, the active ingredient can be released as described, for example, in Pharmaceutical Research, 2(6): 318 (1986) by electrotransport or iontophoresis.

Furthermore, suitable pharmaceutical compositions containing a compound of formula (I) can also be administered in fom of a pill, lacquered tablet, sugar-coated tablet, hard or soft gelatin capsule, syrup, tincture, cream, lotion, nasal spray, aerosol mixture, microcapsule, implant or rod.

The following preparations serve to illustrate the invention without restricting it, however.

EXAMPLE A

| Soft gelatin capsules containing 100 mg of active ingredient per capsule: | |
| --- | --- |
|  | per capsule |
| Active ingredient | 100 mg |
| Triglyceride mixture fractionated from coconut fat | 400 mg |
| Capsule contents | 500 mg |

EXAMPLE B

| Emulsion containing 60 mg of active ingredient per 5 ml: | |
| --- | --- |
|  | per 100 ml emulsion |
| Active ingredient | 1.2 g |
| Neutral oil | q.s. |
| Sodium carboxymethylcellulose | 0.6 g |
| Polyoxyethylene stearate | q.s. |
| Glycerol, pure | 0.2 to 2.0 g |
| Flavoring | q.s. |
| Water (deionized or distilled) | ad 100 ml |

EXAMPLE C

| Rectal pharmaceutical form containing 40 mg of active ingredient per suppository: | |
| --- | --- |
|  | per suppository |
| Active ingredient | 40 mg |
| Suppository base | ad 2 g |

EXAMPLE D

| Tablets containing 40 mg of active ingredient per tablet: | |
| --- | --- |
|  | per tablet |
| Lactose | 600 mg |
| Corn starch | 300 mg |

-continued

Tablets containing 40 mg of active ingredient per tablet:

| | per tablet |
|---|---|
| Soluble starch | 20 mg |
| Magnesium stearate | 40 mg |
| | 1000 mg |

EXAMPLE E

Coated tablets containing 50 mg of active ingredient per coated tablet:

| | per coated tablet |
|---|---|
| Active ingredient | 50 mg |
| Corn starch | 100 mg |
| Lactose | 60 mg |
| Sec. calcium phosphate | 30 mg |
| Soluble starch | 5 mg |
| Magnesium stearate | 10 mg |
| Colloidal silica | 5 mg |
| | 260 mg |

EXAMPLE F

The following formulas are suitable for producing the contents of hard gelatin capsules:

| a) | Active ingredient | 100 mg |
|---|---|---|
| | Corn starch | 300 mg |
| | | 400 mg |

| b) | Active ingredient | 140 mg |
|---|---|---|
| | Lactose | 180 mg |
| | Corn starch | 180 mg |
| | | 500 mg |

EXAMPLE G

Drops can be produced in accordance with the following formula (100 mg of active ingredient in 1 ml = 20 drops):

| Active ingredient | 10 g |
|---|---|
| Methyl benzoate | 0.07 g |
| Ethyl benzoate | 0.03 g |
| Ethanol 96% pure | ad 100 ml |

This invention also relates to intermediates of compounds according to the general formula (I). Intermediates according to this invention are described by general formula (III),

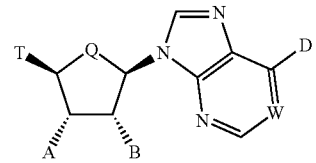

(III)

wherein:
W is N, N→O, or CH;
Q is $CH_2$ or O;
D is halogen;
T is a residue selected from the group consisting of $C_1$-$C_{10}$-alkyl, $C_1$-$C_{10}$-cycloalkyl, aryl-($C_1$-$C_{10}$-alkylene)- and heterocyclyl-($C_1$-$C_{10}$-alkylene), which residues are monosubstituted by halogen or $OR_2$, and which residues can be optionally substituted by at least one substituent selected from the group consisting of halogens, psendohalogens, mercapto, $NH_2$, nitro, hydroxy, unsubstituted and at least monosubstituted $C_1$-$C_6$-alkyl, $C_1$-$C_6$-alkoxy, ($C_1$-$C_6$-alkyl)amino, aryl and heterocyclyl, the substituents of which are selected from the group consisting of halogens, pseudohalogens, $C_1$-$C_3$-alkyl, $C_1$-$C_3$-alkoxy and hydroxy;
$R^2$ is selected from the group consisting of $C_1$-$C_{10}$-alkyl substituted by at least one substituent selected from halogens, $C_1$-$C_6$-alkyl-S(O)$_2$— and ($C_1$-$C_6$-alkyl)thio-C(S)—;
A is hydrogen, $C_1$-$C_{10}$-alkyl, hydroxy-($C_1$-$C_{10}$-alkylene)-, $C_1$-$C_{10}$-alkoxy-($C_1$-$C_{10}$-alkylene)-, or OR';
B ist hydrogen, $C_1$-$C_{10}$-alkyl, hydroxy-($C_1$-$C_{10}$-alkylene)-, $C_1$-$C_{10}$-alkoxy-($C_1$-$C_{10}$-alkylene)-, or OR";
R' and R" are independently selected from the group consisting of hydrogen, $C_1$-$C_6$-alkyl, aryl-($C_1$-$C_6$-alkylene)-, ($C_1$-$C_6$-alkyl)-CO, carbalkoxy, aryl-($C_1$-$C_6$-alkylene)-CO—, and aryl-O—CO—;
when A and B are OR' and OR", respectively, R' and R" may together form a substituent selected from the group consisting of

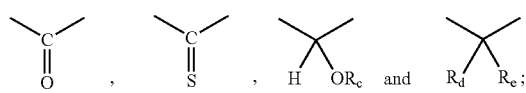

$R_C$ is hydrogen or $C_1$-$C_6$-alkyl;
$R_d$ and $R_e$ are independently hydrogen, $C_1$-$C_{10}$-alkyl, or together with the carbon atom to which they are attached may form a 1,1-cycloalkyl group;
heterocyclyl is a 4 to 10-membered, mono- or bicyclic heterocycle containing one or more heteroatoms selected from the group consisting of N, O and S;
aryl is phenyl, indan-1-yl, indan-2-yl, naphth-1-yl or naphth-2-yl;
or a pharmaceutically acceptable salt thereof, a pharmaceutically acceptable prodrug thereof, an N-oxide thereof, a hydrate thereof or a solvate thereof;
with the proviso that, in case Q is O and D is chlorine, T is not methyl monosubstituted by halogen; in case Q is O, A and B are both hydroxy and D is chlorine, T is not $C_1$-$C_6$-alkyl substituted by fluorine; in case Q is O, A and B are both hydroxy and D is chlorine, $R^2$ is not $C_1$-$C_6$-akyl substituted by fluorine.

Preferred compounds of the formula (III) are these compounds in which one or more of the residues contained therein have the meanings given below, with all combinations of preferred substitutent definitions being a subject of the present invention. With respect to all preferred compounds of the formula (III) the present invention also includes all pharmaceutically acceptable salts thereof, pharmaceutically acceptable prodrugs thereof, N-oxides thereof, hydrates thereof or solvates thereof.

In preferred embodiments of the present invention, the substituents A, B, D, Q, T and W of the formula (III) indepentently from each other have the following meanings. Hence, one or more of the subtituents A, B, D, Q, T and W can have the preferred meanings, the more preferred meanings, the even more preferred meanings, the much more preferred meanings and/or the most preferred meanings given below.

W is preferably N;
Q is preferably $CH_2$;
D is preferably chlorine or fluorine, D is most preferably chlorine;
T is preferably $C_1$-$C_{10}$-alkyl which is monosubstituted by halogen or $OR^2$, and which $C_1$-$C_{10}$-alkyl can furthermore be optionally substituted by at least one substituent selected from the group consisting of halogens, psendohalogens, mercapto, $NH_2$, nitro, hydroxy, unsubstituted and at least monosubstituted $C_1$-$C_6$-alkyl, $C_1$-$C_6$-alkoxy, ($C_1$-$C_6$-alkyl)amino, aryl and heterocyclyl, the substituents of which are selected from the group consisting of halogens, pseudohalogens, $C_1$-$C_3$-alkyl, $C_1$-$C_3$-alkoxy and hydroxy;
T is more preferably $C_1$-$C_{10}$-alkyl substituted by at least one substituent selected from halogens and $OR^2$; T is even more preferably fluoromethyl, trifluoromethoxymethyl, difluoromethoxymethyl, $CH_3SC(S)$—O—$CH_2$— or $CH_3S(O)_2$—O—$CH_2$—; T is much more preferably fluoromethyl, trifluoromethoxymethyl or difluoromethoxymethyl; T is most preferably fluoromethyl;
A is preferably OR';
B is preferably OR";
Preferably, R' and R" are both hydrogen or R' and R" together preferably form a substituent selected from the group consisting of

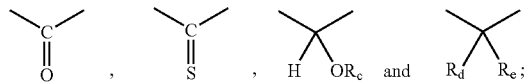

R' and R" together more preferably form

$R_c$ is preferably hydrogen or methyl;
$R_d$ and $R_e$ are preferably independently hydrogen, or $C_1$-$C_6$-alkyl, $R_d$ and $R_e$ are more preferably both $C_1$-$C_3$-alkyl; $R_d$ and $R_e$ are even more preferably both methyl.

Compounds of the formula (III) in which some or all of the above-mentioned groups have the preferred meanings, the more preferred meanings or the most preferred meanings defined above are also an object of the present invention.

Most preferred compounds according to the general formula (III) are selected from the group consisting of 6-chloro-9-((3aS,4R,6S,6aR)-6-fluoromethyl-2,2-dimethyl-tetrahydro-cyclopenta-1,3-dioxol-4-yl)-9H-purine,
6-fluoro-9-((3aS,4R,6S,6aR)-6-fluoromethyl-2,2-dimethyl-tetrahydro-cyclopenta-1,3-dioxol-4-yl)-9H-purine,
6-chloro-9-((1R,2S,3R,5R)-5-fluoromethyl-1,2-dihydroxy-cyclopent-3-yl-)-9H-purine, 6-fluoro-9-((1R,2S,3R,5R)-5-fluoromethyl-1,2-dihydroxy-cyclopent-3-yl-)-9H-purine,
6-chloro-9-((3aS,4R,6S,6aR)-6-trifluoromethoxymethyl-2,2-dimethyl-tetrahydro-cyclopenta-1,3-dioxol-4-yl)-9H-purine, 6-fluoro-9-((3aS,4R,6S,6aR)-6-trifluoromethoxymethyl-2,2-dimethyl-tetrahydrocyclo-penta-1,3-dioxol-4-yl)-9H-purine, 6-chloro-9-((1R,2S,3R,5R)-5-trifluoromethoxymethyl-1,2-dihydroxy-cyclopent-3-yl-)-9H-purine and 6-fluoro-9-((1R,2S,3R,5R)-5-trifluoro-methoxymethyl-1,2-dihydroxy-cyclopent-3-yl-)-9H-purine, or a pharmaceutically acceptable salt thereof, a pharmaceutically acceptable prodrug thereof, an N-oxide thereof, a hydrate thereof or a solvate thereof.

Compounds of this invention may be prepared following the scheme drawn below:

Compounds of formula I, wherein W=N, Q is $CH_2$ and T is $CH_2F$ are prepared starting with the product of Reaction Scheme A. In this reaction, 6-chloroaristeromycine, with the 1 and 2 hydroxyl groups of the carbocycle protected (protecting group P), is treated with a sulfonyl derivative, for example methanesulfonyl chloride, and the product sulfonate treated with a suitable fluoride source, for example tetrabutylammonium fluoride, to yield the 5-fluoromethyl derivative.

REACTION SCHEME A

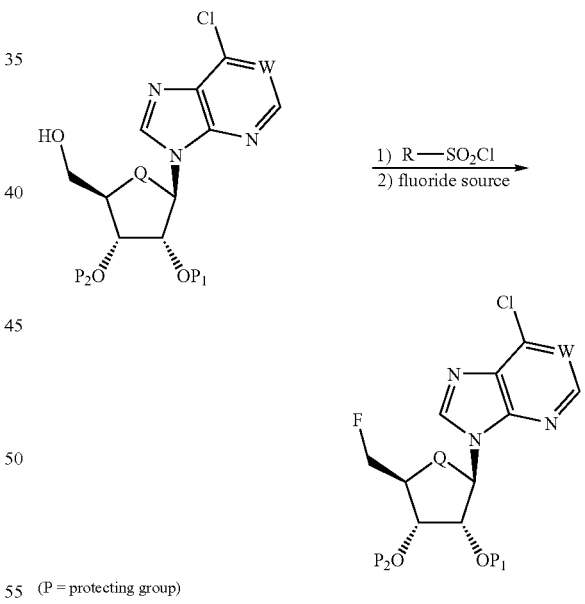

(P = protecting group)

Compounds of formula I, wherein W=N, Q is $CH_2$ and T is $CH_2OCF_3$ are prepared starting with the product of Reaction Scheme B. In this reaction, 6-chloroaristeromycine, with the 1 and 2 hydroxyl groups of the carbocycle ring protected, is treated with $CS_2$ and an alkylating agent, for example $CH_3I$, in the presence of aqueous alkaline hydroxide salt, for example a 50% solution of NaOH and a phase transfer agent, for example tetrabutylammonium hydrogensulfate, and the product thiocarbonate treated with a suitable fluoride source, for example hydrogen fluoride pyridine complex, and a suitable electrophile source, for example 1,3-dibromo-5,5-dimethyl hydantoin, to yield the 5-trifluoromethyl derivative.

REACTION SCHEME B

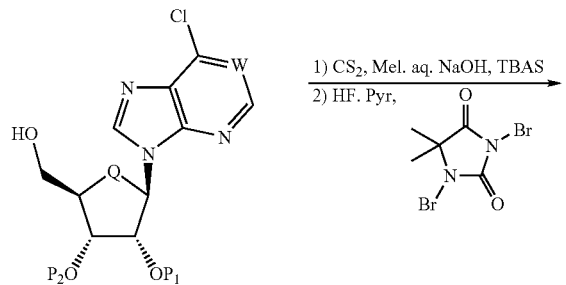

(P = protecting group)

The N6-substituted adenosine and carbocyclic adenosine analogues of the invention may be formed by reacting 6-halopurine riboside or the products of Reaction Schemes A or B with various appropriate amines, as exemplified in Reaction Scheme C. 6-halopurine is preferably 6-fluoropurine or 6-chloropurine.

REACTION SCHEME C

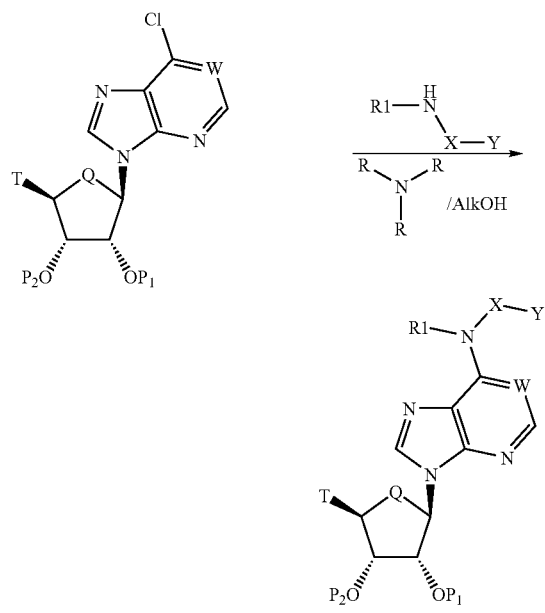

Where X and Y are as defined hereinabove, or protected derivatives thereof.

Compounds of the present invention wherein W is N→O, i.e. the N-oxides, may be prepared by oxidation of the corresponding adenosine or carbocyclic adenosine analogue by known methods, for example by treatment with hydrogen peroxide in acetic acid.

Functional groups of starting compounds and intermediates that are used to prepare the compounds of the invention may be protected by common protecting groups (P) known in the art. Conventional protecting groups for amino and hydroxyl functional groups are described, for example, in T. W. Greene, "Protective Groups in Organic Synthesis", Wiley, New York (1984).

Hydroxyl groups may be protected as esters, such as acyl derivatives, or in the form of ethers. Hydroxyl groups on adjacent carbon atoms may advantageously be protected in the form of ketals or acetals. In practice, the adjacent 1 and 2 hydroxyl groups of the starting compounds in Reaction Schemes A and B are conveniently protected by forming the 1,2 isopropylidene derivatives. The free hydroxyls may be restored by acid hydrolysis, for example, or other solvolysis or hydrogenolysis reactions commonly used in organic chemistry.

Following synthesis, compounds of the invention are typically purified by medium pressure liquid chromatography (MPLC), flash chromatography or column chromatography through a silica gel or Florisil matrix, followed by crystallization. For compounds of formula I typical solvent systems include chloroform:methanol, ethyl acetate:hexane, and methylene chloride:methanol. Eluates may be crystallized from methanol, ethanol, ethyl acetate, hexane or chloroform, etc.

Compounds requiring neutralization may be neutralized with a mild base such as sodium bicarbonate, followed by washing with methylene chloride and brine. Products which are purified as oils are sometimes triturated with hexane/ethanol prior to final crystallization.

The present invention will now be illustrated and explained by the following examples.

EXAMPLE 1

Preparation of (1R,2S,3R,5S)-3-{6-[1-(3-chloro-phenyl-1-yl)-pyrrolidin-3(S)-ylamino]-purin-9-yl}-5-fluoromethyl-cyclopentane-1,2-diol Step 1: Prepartion of 3(S)-3-(1,3-dioxo-1,3-dihydro-isoindol-2-yl-pyrrolidin)-tert-butyloxycarbamate:

To a cold (0° C.) solution of 3(R)-hydroxy-pyrrolidine-1-carboxylic acid, tert-butyl ester (5 gr, 24.03 mmoles) in THF (15 ml) was added PPh₃ (7.25 gr, 27.64 mmoles) and phtalimide (4.07 gr, 27.64 mmoles). To the resulting white suspension was added drop wise a solution of DIAD (5.73 ml, 27.64 mmoles) in THF (15 ml), and the resulting yellow solution was warmed up to room temperature and stirred for 17 hours. The solution was then treated with water (30 ml) and 100 ml of a saturated aqueous solution of K₂CO₃, the aqueous layer was separated and extracted two times with EtOAc. The combined organic layers are washed with brine and dried over magnesium sulfate. The filtrate is concentrated under reduced pressure to give a residue which is purified by flash chromatography on silica gel eluting with 25% to 35% EtOAc in cyclohexane to yield 3(S)-3-(1,3-dioxo-1,3-dihydro-isoindol-2-yl-pyrrolidin)-tert-butyloxycarbamate as a white solid.

Step 2: 3(S)-3-(1,3-dioxo-1,3-dihydro-isoindol-2-yl)-pyrrolidine hydrochloride

3(S)-3-(1,3-dioxo-1,3-dihydro-isoindol-2-yl-pyrrolidin)-tert-butyloxycarbamate (6.2 gr, 17.64 mmoles) was dissolved in a 4 M solution of HCl in dioxane (60 ml) and the suspension was stirred 2 hours at room temperature. $Et_2O$ was added, the solid was collected by filtration, washed 4 times with $Et_2O$ and dried under vacuum to yield 3(S)-3-(1,3-dioxo-1,3-dihydro-isoindol-2-yl)-pyrrolidine hydrochloride as a white solid.

Step 3: 3(S)-3-[1-(3-chlorophenyl)-pyrrolidin-3-yl]-isoindol-1,3-dione

3(S)-3-(1,3-dioxo-1,3-dihydro-isoindol-2-yl)-pyrrolidine hydrochloride (500 mg, 1.98 mmoles), $NEt_3$ (833 µl, 5.94 mmoles), 3-chlorophenyl-boronic acid (638 mg, 3.96 mmoles) and $Cu(OAc)_2$ (359 mg, 1.98 mmoles) were combined in $CH_2Cl_2$ (11 ml) and the blue suspension was stirred at air for 17 hours. The green suspension was then treated with a saturated aqueous solution of $NH_4Cl$ (30 ml), the aqueous layer was separated and extracted three times with EtOAc. The combined organic layers were washed with a saturated aqueous solution of $NH_4Cl$ and dried over magnesium sulfate. The filtrate was concentrated under reduced pressure to give a residue which was purified by flash chromatography on silica gel eluting with 22% EtOAc in cyclohexane to yield 3(S)-3-[1-(3-chlorophenyl)-pyrrolidin-3-yl]-isoindol-1,3-dione as a yellow oil.

Step 4: Preparation of 1-(3-Chloro-phenyl)-pyrrolidin-3(S)-ylamine hydrochloride 3(S)-3-[1-(3-chlorophenyl)-pyrrolidin-3-yl]-isoindol-1,3-dione (630 mg, 1.74 mmoles) and hydrazine hydrate (252 µl, 5.21 mmoles) were combined in EtOH (25 ml) and heated to reflux for 3 hours. The suspension was then cooled to room temperature, the solid was filtered off, washed 3 times with EtOH, the filtrate was evaporated to dryness, partitioned between aqueous 1N HCl (10 ml), water (30 ml) and EtOAc, the aqueous layer was separated and extracted three times with EtOAc, made alkaline with 5N aqueous NaOH, extracted three times with EtOAc and the basic extract was washed with brine and dried over magnesium sulfate. The filtrate was concentrated under reduced pressure to give a residue which was taken up in 10 ml of a 4N HCl solution in dioxane and $Et_2O$ (10 ml); the solution was evaporated to dryness and the residue dried under vacuum to yield 1-(3-Chloro-phenyl)-pyrrolidin-3(S)-ylamine hydrochloride as a brown foam.

Step 5: Preparation of methanesulfonic Acid (3aR,4R,6R,6aS)-6-(6-chloro-purin-9-yl)-2,2-dimethyl-tetrahydro-cyclopenta-1,3-dioxol-4-ylmethyl ester 6-Chloroaristeromycine acetonide (324 mg, 1 mmole) is dissolved in 8 ml of pyrdine, the solution is cooled to 0° C. and methanesulfonyl chloride (120 µl, 1.5 mmoles) was added dropwise. The reaction mixture was then stirred for 1 hour at 0° C., allowed to warm to room temperature and the suspension was stirred vigorously for 1 hour. The solvent was then evaporated to dryness and the residue was partitioned between water and EtOAc, the aqueous layer was separated and extracted twice with EtOAc. The combined organic layers were washed with brine and dried over magnesium sulfate. The filtrate was concentrated under reduced pressure to yield methanesulfonic acid (3aR,4R,6R,6aS-6-(6-chloro-purin-9-yl)-2,2-dimethyl-tetrahydro-cyclopenta-1,3-dioxol-4-ylmethyl ester as a yellow oily residue, used directly in the next step.

Step 6: Preparation of 6-chloro-9-((3aS,4R,6S,6aR)-6-fluoromethyl-2,2-dimethyl -tetrahydro-cyclopenta-1,3-dioxol-4-yl)-9H-purine Methanesulfonic acid (3aR,4R,6R,6aS)-6-(6-chloro-purin-9-yl)-2,2-dimethyl-tetrahydro -cyclopenta-1,3-dioxol-4-ylmethyl ester (402 mg, 1 mmole) prepared as described above and tetrabutylammonium fluoride (hereafter TBAF) as a 1M solution in THF (3 ml, 3 mmoles) are combined in THF (10 ml) and the brown solution was stirred overnight at room temperature. The solvent was then evaporated to dryness and the residue was partitioned between water and EtOAc, the aqueous layer was separated and extracted twice with EtOAc. The combined organic layers were washed with brine and dried over magnesium sulfate. The filtrate was concentrated under reduced pressure to give a residue which is purified by flash chromatography on silica gel eluting with 40% EtOAc in cyclohexane to yield 6-chloro-9-((3aS,4R,6S,6aR)-6-fluoromethyl-2,2-dimethyl-tetrahydro -cyclopen-1,3-dioxol-4-yl)-9H-purine together with 6-fluoro-9-((3aS,4R,6S,6aR)-6-fluoromethyl-2,2-dimethyl-tetrahydro-cyclopenta-1,3-dioxol-4-yl)-9H-purine as an approximately 1 to 1 mixture of compounds, used as such in the next step.

Step 7: Preparation of [(S)-1-(3-chloro-phenyl)-pyrrolidin-3-yl]-[9-((3aS,4R,6S,6aR)-6-fluoromethyl-2,2-dimethyl-tetrahydro-cyclopenta-1,3-dioxol-4-yl)-9H-purin-6-yl]-amine 1-(3-Chloro-phenyl)-pyrrolidin-3(S)-ylamine hydrochloride (300 mg, 1.29 mmoles) prepared as in step 4 of example 1 and 6-chloro-9-((3aS,4R,6S,6aR)-6-fluoromethyl-2,2-dimethyl-tetrahydro-cyclopenta-1,3-dioxol-4-yl)-9H-purine (420 mg, 1.29 mmoles) prepared as described above were combined in EtOH (12 ml), $NEt_3$ (730 µl, 5.15 mmoles) was then added and the resulting brown solution was stirred at reflux under an argon atmosphere. After 22 h, the reaction mixture was cooled to room temperature, evaporated to dryness, the residue was partitioned between water and EtOAc, the aqueous layer was separated and extracted two times with EtOAc. The combined organic layers are washed with brine and dried over magnesium sulfate. The filtrate is concentrated under reduced pressure to give a residue which is purified by flash chromatography on silica gel eluting with 40% EtOAc in cyclohexane followed by 5% MeOH in $CH_2Cl_2$ to yield [(S)-1-(3-chloro-phenyl)-pyrrolidin-3-yl]-[9-((3aS,4R,6S,6aR)-6-fluoromethyl-2,2-dimethyl -tetrahydro-cyclopenta-1,3-dioxol-4-yl)-9H-purin-6-yl]-amine Step 8: (1R,2S,3R,5S)-3-{6-[1-(3-chloro-phenyl-1-yl)-pyrrolidin-3(S) -ylamino]-purin-9-yl}-5-fluoromethyl-cyclopentane-1,2-diol

[(S)-1-(3-chloro-phenyl)-pyrrolidin-3-yl]-[9-((3aS,4R,6S,6aR)-6-fluoromethyl-2,2-dimethyl-tetrahydro-cyclopenta-1,3-dioxol-4-yl)-9H-purin-6-yl]-amine (250 mg, 0.5 mmole) prepared as described above was put in solution in THF (8 ml) and the resulting solution was treated with 12 N HCl in water (500 µl, 6 mmoles), and stirred for 2 h at room temperature. The solvent was then evaporated to dryness and the residue was dried under vacuum to yield (1R,2S,3R,5S)-3-{6-[1-(3-chloro-phenyl-1-yl)-pyrrolidin-3(S) -ylamino]-purin-9-yl}-5-fluoromethyl-cyclopentane-1,2-diol as its dihydrochloride salt. $^1$H NMR (400 MHz, $(CD_3)_2SO$ d6, at 353K, δ in ppm): from 1.75 to 1.95 (mt: 1H); from 2.15 to 2.55 (mt: 4H); from 3.30 to 3.50 (mt: 2H); 3.54 (mt: 1H); 3.73 (dd, J=10 and 6.5 Hz: 1H); 3.96 (mt: 1H); 4.38 (dd, J=9 and 6 Hz: 1H); 4.56 (d mt, $J_{HF}$=47.5 Hz: 2H); 4.86(mt: 1H); 5.18 (mf: 1H); 6.54 (large d, J=8 Hz: 1H); 6.57 (large s: 1H); 6.65 (large d J=8 Hz: 1H); 7.18 (t, J=8 Hz: 1H); 8.47 (s: 1H); 8.63 (s: 1H); from 9.10 to 9.50 (mf: 1H).

EXAMPLE 2

Preparation of (1R,2S,3R,5S)-3-{6-[(R)-1-(3-chloro-thiophen-2-ylmethyl) -propylamino]-purin-9-yl}-5-fluoromethyl-cyclopentane-1,2-diol:

Step 1: Preparation of [(R)-1-(3-chloro-thiophen-2-ylmethyl)-propyl]-[9-((3aS,4R,6S,6aR)-6-fluoromethyl-2,2-dimethyl-tetrahydro-cyclopenta-1,3-dioxol-4-yl)-9H-purin-6-yl]-amine (R)-1-(3-Chloro-thiophen-2-ylmethyl)-propylamine hydrochloride (1.36 g, 6 mmoles) and 6-chloro-9-((3aS,4R, 6S,6aR)-6-fluoromethyl-2,2-dimethyl-tetrahydro -cyclopenta-1,3-dioxol-4-yl)-9H-purine (1.63 g, 5 mmoles) prepared as described above were combined in nBuOH (40 ml), $^i$Pr$_2$NEt (3.5 ml, 20 mmoles) was then added and the resulting solution was stirred at reflux under an argon atmosphere. After 5 h, the reaction mixture was cooled down to room temperature, partitioned between water, brine and EtOAc, the aqueous layer was separated and extracted two times with EtOAc. The combined organic layers were washed with brine and dried over sodium sulfate. The filtrate is concentrated under reduced pressure to give a residue which was purified by flash chromatography on silica gel eluting with 2% MeOH in CH$_2$Cl$_2$ to yield [(R)-1-(3-chloro-thiophen-2-ylmethyl)-propyl]-[9-((3aS,4R,6S,6aR)-6-fluoromethyl-2,2-dimethyl -tetrahydro-cylopenta-1,3-dioxol-4-yl)-9H-purin-6-yl]-amine Step 2: (1R,2S,3R,5S)-3-{6-[(R)-1-(3-chloro-thiophen-2-ylmethyl) -propylamino]-purin-9-yl}-5-fluoromethyl-cyclopentane-1,2-diol:

[(R)-1-(3-chloro-thiophen-2-ylmethyl)-propyl]-[9-((3aS,4R,6S,6aR)-6-fluoromethyl-2,2-dimethyl-tetrahydro-cyclopenta-1,3-dioxol-4-yl)-9H-purin-6-yl]-amine (1.23 g, 2.56 mmoles) prepared as described above was put in solution in THF (31 ml) and the resulting solution was treated with 12 N HCl in water (2.56 ml, 30.7 mmoles), and stirred for 2 h at room temperature. The solvent was then evaporated to dryness and the residue partitioned between water and AcOEt and neutralized with a saturated bicarbonate solution, the aqueous layer was separated and extracted twice with EtOAc. The combined organic layers were washed with brine and dried over sodium sulfate. The filtrate was concentrated under reduced pressure to give a residue which was taken up in $^i$Pr$_2$O and the resulting solution is diluted with pentane, the solid was filtrated, washed with pentane 3 times and dried to yield (1R,2S,3R,5S)-3-{6-[(R)-1-(3-chloro-thiophen-2-ylmethyl) -propylamino]-purin-9-yl}-5-fluoromethyl-cyclopentane-1,2-diol. $^1$H NMR (300 MHz, (CD$_3$)$_2$SO d6, δ in ppm): 0.92 (t, J=7,5 Hz: 3H); 1.68 (mt: 2H); 1.84 (mt: 1H); 2.31 (mt:2H); 3.13 (mt:2H); 3.92 (mt: 1H); 4.40 (mt: 1H); 4.51 (mf: 1H); 4.55 (dmt, J$_{HF}$=48 Hz: 2H); 4.75 (mt: 1H); 4.94 (d, J=3,5 Hz: 1H); 5.10 (d, J=6 Hz: 1H); 6.98 (d, J=5 Hz: 1H); 7.43 (d, J=5 Hz: 1H); 7.72 (broad d, J=8 Hz: 1H); 8.18 (mf: 1H); 8.23 (s:1H). m.p.=143°.

EXAMPLE 3

Preparation of (1R,2S,3R,5R)-3-{6-[1-(3-chloro-phenyl-1-yl)-pyrrolidin-3(S)-ylamino]-purin-9-yl}-5-trifluoromethoxymethyl-cyclopentane-1,2-diol Step 1: Preparation of Dithiocarbonic Acid O-[(3aR,4R,6R, 6aS)-6-(6-chloro-purin-9-yl) -2,2-dimethyl-tetrahydro-cyclopenta-1,3-dioxol-4-ylmethyl]ester S-methyl ester:

To a solution of 6-chloroaristeromycine acetonide (1 gr, 3.08 mmoles) in toluene (12 ml) was sequentially added CS$_2$ (3.1 ml, 51.3 mmoles), Bu$_4$NHSO$_3$ (1.05 gr, 3.08 mmoles), MeI (211 μl, 3.39 mmoles), and NaOH (3.08 ml of a 50% aqueous solution, 38.5 mmoles). The resulting white suspension was vigorously stirred at room temperature for 90 minutes. 10 ml of toluene and 30 ml of water was then added, the aqueous layer was separated and extracted three times with EtOAc. The combined organic layers were washed with water and dried over magnesium sulfate. The filtrate was concentrated under reduced pressure to give a residue which was dried under vacuum to give dithiocarbonic acid 0-[(3aR,4R,6R,6aS)-6-(6-chloro-purin-9-yl)-2,2-dimethyl-tetrahydro-cyclopenta-1,3-dioxol-4-ylmethyl]ester S-methyl ester as a gummy yellow solid.

Step 2: Prepartion of (1R,2S,3R,5R)-3-(6-chloro-purin-9-yl)-5-trifluoromethoxymethyl -cyclopentane-1,2-diol To a cooled (−78° C.) suspension of 1,3-dibromo-5,5-dimethyl hydantoin (1.26 gr, 9.24 mmoles) in CH$_2$Cl$_2$ (25 ml) was added HF×Pyridine complex (6 ml), and dithiocarbonic acid 0-[(3aR,4R,6R,6aS)-6-(6-chloro-purin-9-yl)-2,2-dimethyl-tetrahydro -cyclopenta-1,3-dioxol-4-ylmethyl]ester S-methyl ester (1.28 gr, 3.08 mmoles), prepared as described in step 1, in CH$_2$Cl$_2$ (10 ml). The resulting mixture was stirred 15 minutes at −78° C., then warmed up to 0° C. over 1 hour. The reaction mixture was then poured onto a mixture of 180 ml of a saturated aqueous solution of NaHCO$_3$ and 50 ml of a 50% aqueous solution of Na$_2$SO$_3$, stirred for 20 minutes, then extracted 4 times with CH$_2$Cl$_2$. The combined organic layers were washed with water and dried over magnesium sulfate. The filtrate was concentrated under reduced pressure to give a residue which was purified by flash chromatography on silica gel eluting with 14% Cyclohexane in EtOAc, followed by 10% MeOH in CH$_2$Cl$_2$ to yield (1R,2S,3R,5R)-3-(6-chloro-purin-9-yl)-5-trifluoromethoxymethyl-cyclopentane-1,2-diol as a brown foam.

Step 3: Preparation of (1R,2S,3R,5R)-3-{6-[1-(3-chloro-phenyl-1-yl) -pyrrolidin-3(S) -ylamino]-purin-9-yl}-5-trifluoromethoxymethyl-cyclopentane-1,2-diol To a solution of 1-(3-Chloro-phenyl)-pyrrolidin-3(S)-ylamine hydrochloride (130 mg, 0.55 mmole) prepared as in step 4 of example 1, in EtOH (14 ml) was added NEt$_3$ (196 μl, 1.4 mmoles), followed by (1R,2S,3R,5R)-3-(6-chloro-purin-9-yl)-5-trifluoromethoxymethyl-cyclopentane-1,2-diol prepared as above (182 mg, 0.46 mmole), and the resulting solution was stirred at reflux for 24 hours. The solvent was then evaporated to dryness and the residue partitioned between water and AcOEt. The aqueous layer was separated and extracted twice with EtOAc. The combined organic layers were washed with brine and dried over magnesium sulfate to give a residue which was purified by flash chromatography on silica gel eluting with EtOAc, followed by 8% MeOH in CH$_2$Cl$_2$ to yield a solid which was re-purified by preparative LC-MS. The fractions containing the compound was taken up in water and NaHCO$_3$ solution and extracted twice with EtOAc. The combined organic layers were washed with brine and dried over magnesium sulfate to yield (1R,2S,3R,5R)-3-{6-[1-(3-chloro-phenyl-1-yl) -pyrrolidin-3(S) -ylamino]-purin-9-yl}-5-trifluoromethoxymethyl-cyclopentane-1,2-diol as a yellow oily residue. $^1$H NMR (300 MHz, (CD$_3$)$_2$SO d6, δ in ppm): 1.82 (mt: 1H); 2.21 (mt: 1H); from 2.25 to 2.45 (mt: 3H); from 3.25 to 3.40 (mt: 2H); 3.48 (mt: 1H); 3.66 (mt: 1H); 3.91 (mt: 1H); 4.23 (mt: 2H); 4.43 (mt: 1H); 4.77 (mt: 1H); from 4.80 to 5.05 (broad mf: 1H); 5.01 (d, J=4.5 Hz: 1H); 5.12 (d, J=6 Hz: 1H); 6.51 (mt: 2H); 6.62 (broad d, J=8 Hz: 1H); 7.18 (t, J=8 Hz: 1H); 8.05 (mf: 1H); 8.27 (s:2H).

EXAMPLE 4

(1R,2S,3R,5S)-3-{6-[1-(5-trifluoromethyl-pyridin-2-yl)-pyrrolidin-3(S)-ylamino]-purin-9-yl}-5-fluoromethyl-cyclopentane-1,2-diol, $^1$H NMR (300 MHz, $(CD_3)_2SO$ d6, δ in ppm): from 1.75 to 1.95 (mt: 1H); from 2.20 to 2.55 (mt: 4H); from 3.60 to 3.85 (mt: 3H); from 3.90 to 4.05 (mt: 2H); 4.37 (dd, J=9 and 5.5 Hz: 1H); 4.55 (dd. J=47.5 and 5.5 Hz: 2H); from 4.80 to 5.00 (mt: 2H); 6.79 (large d. J=9 Hz: H); 7.93 (broad d. J=9 Hz: 1H); 8.41 (broad s: 1H); 8.51 (mf: 1H); 8.69 (s: 1H); from 9.50 to 10.00 (mf: 1H).

EXAMPLE 5

(1R,2S,3R,5S)-3-{6-[1-cyclopent-1-ylamino]-purin-9-yl}-5-fluoromethyl-cyclopentane-1,2-diol

EXAMPLE 6

(1R,2S,3R,5S)-3-{6-[1-(5-chloro-pyridin-2-yl)-pyrrolidin-3(S) -ylamino]-purin-9-yl}-5-fluoromethyl-cyclopentane-1,2-diol. $^1$H NMR (300 MHz. $(CD_3)_2SO$ d6. δ in ppm): from 1.75 to 1.95 (mt: 1H); from 2.20 to 2.55 (mt: 4H); from 3.55 to 3.80 (mt: 3H); 3.92 (mt: 2H); 4.37 (dd. J=9 and 6 Hz: 1H); 4.53 (dd. J=47.5 and 5 Hz: 2H); 4.87 (mt: 1H); 4.96 (mf: 1H); 6.84 (large d. J=8.5 Hz: 1H); 7.81 (broad d. J=8.5 Hz: 1H); 8.13 (d. J=2.5 Hz: 1H); 8.50 (mf: 1H); 8.69 (s: 1H); from 9.40 to 10.00 (mfs: 1H).

EXAMPLE 7

(1R,2S, 3R, 5S)-3-{6-[1-(4-trifluoromethyl-phenyl-1-yl)-pyrrolidin-3(S)-ylamino]-purin-9-yl}-5-fluoromethyl-cyclopentane-1,2-diol, m.p.: 178° C.

EXAMPLE 8

(1R,2S,3R,5R)-3-{6-[1-(5-trifluoromethyl-pyridin-2-yl)-pyrrolidin -3(s)-ylamino]-purin-9-yl}-5-trifluoromethoxymethyl-cyclopentane-1,2-diol, m.p.: 142° C.

EXAMPLE 9

(1R,2S,3R,5R)-3-{6-[1-(5-chloro-pyridin-2-yl)-pyrrolidin-3(S) -ylamino]-purin-9-yl}-5-trifluoromethoxymethyl-cyclopentane-1,2-diol, m.p.: 130°

EXAMPLE 10

(1R,2S,3R,5R)-3-{6-[1-(4-trifluoromethyl-phenyl-1-yl)-pyrrolidin -3(S)-ylamino]-purin-9-yl}-5-trifluoromethoxymethyl-cyclopentane-1,2-diol, m.p.: 153°

EXAMPLE 11

(1R,2S, 3R, 5R)-3-{6-[(R)-1-(3-chloro-thiophen-2-ylmethyl) -propylamino]-purin-9-yl}-5-trifluoromethoxymethyl-cyclopentane-1,2-diol, m.p.: 140°

EXAMPLE 12

6-Chloro-9-((3aS,4R,6R,6aR)-6-difluoromethoxymethyl-2,2-dimethyl-tetrahydro -cyclopenta-1,3-dioxol-4-yl)-9H-purine.

6-Chloroaristeromycine acetonide (5 g, 15.4 mmole), 8 g (122 mmole) zinc powder, and 10 g molecular sieves 3A° was stirred with 100 ml of dichloromethane at room temperature for 30 minutes. 4.5 g (15.4 mmole) $ZnBrCF_3 \cdot 2CH_3CN$ was added and the resulting mixture was stirred overnight at room temperature. Additional 2.2 g (7.5 mmole) $ZnBrCF_3 \cdot 2 CH_3CN$ was added and the mixture was stirred an additional eight hours. Finally, another 2.2 g $ZnBrCF_3 \cdot 2 CH_3CN$ was added, and the mixture was heated at 50° C. for five hours. The mixture was cooled to room temperature, dichloromethane was added and the organic phase was washed with aqueous $NaHCO_3$. The organic layer was dried over $MgSO_4$, filtered and concentrated in vacuo. The residue was chromatographically purified (silica; n-heptane/ethyl acetate 5/1) and yielded 6-chloro-9-((3aS,4R,6R,6aR)-6-difluoromethoxymethyl-2,2-dimethyl-tetrahydro-cyclopenta-1,3-dioxol-4-yl)-9H-purine. $^1$H NMR (500 MHz. $(CDCl_3)$ δ in ppm): 1.35 (s, 3H); 1.6 (s, 3H), 2.55 (m, 3H), 4.05 (m, 2H), 4.7 (m, 1H), 4.85 (m, 1H), 5.05 (m, 1H), 6.30 (t, 1H), 8.1 (s, 1H), 8.75 (s, 1H). This reaction was performed using a teflon apparatus.

Biological Data:

A.

Measurement of Plasma Lipdis (Free Fatty Acids, Triglycerides, Cholesterol) in Anaesthetized Rats:

Plasma lipid levels were assayed in anaesthetized rats. Briefly, rats were anaesthetized with an intraperitoneal injection of pentobarbital sodium (60 mg/kg), tracheotomized, and one jugular vein per rat was cannulated for intravenous administration (bolus injection or infusion). Anesthesia was maintained for up to 7 hours by subcutaneous infusion of pentobarbital sodium (adjusted to the anesthetic depth of the individual animal; about 24 mg/kg/h). Body temperature was monitored with a rectal probe thermometer, and temperature was maintained at 37° C. by means of a heated surgical plate. The rats were allowed to stabilize their blood levels after surgery for up to 2 hours, after which the test compound was injected intraperitoneally. Blood samples for glucose analysis (10 μl) were obtained from the tip of the tail every 15 minutes. For analysis of plasma lipids blood samples (0.3 ml) were obtained from the jugualr vein either every 10 to 15 minutes for up to 2 hours, or every hour for up to 5 hours after compound administration. Standard enzymatic procedures were used to determine blood glucose (Bergmeyer, 1974).

B.

Measurement of Insulin Sensitivity in Conscious Rats:

Insulin resistant Zucker Fatty rats or Zucker Diabetic Fatty (ZDF) rats were treated for up to 3 weeks with the test compound orally once daily. Plasma parameters were obtained by retroorbital bleeding during inhalation anaesthesia on respective study days. At the end of the study rats were starved overnight and they received an insulin bolus injection (3 U/kg s.c.) and blood glucose reduction was monitored up to 6 hours. In the case of improvement of insulin sensitivity by the test compound the blood glucose reduction was much more pronounced and prolonged compared to that of the control group.

C.

In Vitro Functional Assays with Recombinant Cell Lines:

Functional assays were performed by detection of agonist-induced changes in the intracellular concentration of $Ca^{2+}$ in recombinant cell lines expressing adenosine receptor subtypes using the FLIPR™ (fluorescence imaging plate reader, Molecular Devices) technology. To allow optimal signalling through $Ca^{2+}$, chinese hamster ovary (CHO) cells were stably double-transfected with cDNAs to achieve expression of suitable combinations of adenosine receptor subtypes (A1, A2a, A2b or A3) with either G-protein Gα16 or hybrid protein Gαqi4myr (German Patent Application no. 100333532.2). Optimal signals were achieved using combinations as follows:

| (1.) | CHO | Adenosine A1 receptor | Gαqi4myr |
|---|---|---|---|
| (2.) | CHO | Adenosine A2a receptor | Gα16 |
| (3.) | CHO | Adenosine A2b receptor | Gα16 |
| (4.) | CHO | Adenosine A3 receptor | Gαqi4myr |

For assays, recombinant cells were seeded in 96-well dishes (50000 cells/well) and grown overnight. Medium was then removed and cells incubated for 1 hour in buffer containing the dye Fluo-4. After incubation with dye, cells were washed, test compound added and changes in intracellular $Ca^{2+}$ concentration measured by FLIPR. Measured values were expressed as % change relative to controls (0%: no test compound added; 100%: 1 μM Adenosine added) and used for calculation of dose-response curves and subsequent determination of $EC_{50}$ values.

| $EC_{50}$ values (agonist activity at adenosine receptors; μM): | | | | |
|---|---|---|---|---|
| Example | A1 | A2A | A2B | A3 |
| 1 | 0.15 | inactive | >30 | >50 |
| 2 | 0.02 | inactive | 3.4 | >40 |
| 3 | 3.69 | >30 | inactive | inactive |
| 4 | 1.61 | Inactive | >30 | >50 |
| 6 | 1.25 | Inactive | >30 | inactive |
| 7 | 1.25 | Inactive | >30 | >50 |
| 10 | 15.4 | Inactive | inactive | >50 |

D.

Effect on the Isolated Guinea Pig Atrium:

Guinea pigs of either sex were killed by a blow on the back of the neck and exsanguinated.

Their heart was taken out and the atria removed. The preparation (atrium) was immediately transferred to Ringer solution (JT 431) which was at a temperature of 32° C. and was bubbled with a mixture of 95% $O_2$ and 5% $CO_2$. The composition of the solution in g/ml was: NaCl 9.0; KCl 0.42 $CaCl_2$ 0.24; $NaHCO_3$ 0.2; glucose 1.0. The atrium beats spontaneously with an initial tension of 500 mg. The contractile force and the heart rate was recorded with a computer program and automatically calculated (B-mon and A-mon PC programs. Fa. Jäckel. Hanau. GERMANY). After equilibration, the test compound was added to a final bath concentration. N was 4-6 per concentration.

| Effect on contractile force and heart rate: | | |
|---|---|---|
| Example | Contractile force | Heart rate |
| 1 | ±0% at 30 μM | no effect at 1–100 μM |
| 2 | −4% at 10 μM | −4% at 10 μM |
| 4 | −7% at 10 μM | no effect at 1–100 μM |
| 6 | −3% at 30 μM | no effect at 1–100 μM |
| 7 | −1% at 30 μM | no effect at 1–100 μM |
| 10 | +3% at 30 μM | no effect at 1–100 μM |

E.

Antilipolytic Effect in Isolated Rat Adipocytes:

For the preparation of isolated rat adipocytes, epididymal fat pads were obtained from male Sprague-Dawley rats (150-180 g) killed by decapitation. The main fat pad blood vessel was removed with forceps and the pads were cut into small pieces. Digestion was carried out at 37° C. in a shaking water bath by treating 1 g of sliced pad for 20 min with 3 ml of 1 mg/ml collagenase (type I, CLS, Worthington) in 1% BSA, fraction V, in KRH (Krebs-Ringer solution buffered with 25 mM HEPES/KOH, pH 7.4, containing 2.5 mM $CaCl_2$, 2 mM glucose, 1 mM sodium pyruvate, 0.5 units/ml adenosin deaminase and 200 nM phenylisopropyl adenosine). The adipocytes were filtered through nylon mesh of sufficient pore size that no pressure other than gentle teasing with a plastic spatula was necessary for the cells to pass through. After three cycles of centrifugation (500 g, 1 min), aspiration of the infranatant. and resuspension in KRH containing 1% BSA, the cells were suspended in KRH containing 4% defatted BSA. Small aliquots of the final suspension were aspirated into capillary hematocrit tubes and centrifuged for 1 min in a Microhematocrit centrifuge in order to determine what fraction of the suspension consisted of fat cells. Results expressed as activities per unit volume of packed adipocytes (corresponding to equivalent numbers of cells) are based on this centrifugation procedure. Lipolysis was initiated by addition of a 100 μl aliquot of the adipocyte suspension to 700 μl of incubation medium [prewarmed to 37° C. and consisting of KRH, 4% defatted BSA and 1 U/ml adenosine deaminase (type I, Sigma)], with or without addition of 8 μl of a solution of the appropriate test substance in 100% DMSO (at a concentration corresponding to 100 times its concentration in the final mixture). Thus, the final DMSO concentration in the incubation mixture was no greater than 1% and did not affect cell viability (as determined by the sensitivity of the adipocytes in respect of isoproterenol-induced lipolysis and its inhibition by insulin). Incubations were performed in 5 ml polypropylene vials agitated in a shaking water bath (140 cycles/min, amplitude 4.5 cm) at 37° C. for 20, 40, and 60 min. The incubation was terminated by addition of 200 μl of 50 mM EDTA buffered to pH 7.4 with Tris. For the glycerol determination, the whole mixture was mixed rapidly and homogenized with a ground glass pestle in a 1 ml ground glass homogenizing tube (10 pulses). The homogenate was transferred immediately to a 1.5 ml Eppendorf cup precooled to 4° C., after which the extracts were maintained at 4° C. The homogenate was then centrifuged (10,000 g, 15 min) and the infranatant below the fat cake removed with a glass Pasteur pipette. taking care not to aspirate the membrane pellet. and transferred to another Eppendorf cup. 300 μl aliquots of the infranatant were added to 300 μl volumes of 10% (w/v) $HClO_4$. The precipitate was in each case removed by centrifugation (10,000 g, 2 min) and the supernatant neutralized with 20% (w/v) KOH, followed by addition of 50 μl of 1 M Tris/HCl, pH 7.4, A 50 μl sample was then incubated (5 min, 37° C.) with 1 ml of 0.1 M HEPES/KOH, pH 7.5, containing 2 mM ATP, 0.5 mM 4-aminoantipyrine, 1 mM EDTA, 0.5 U glycerol kinase, 4 U glycerol-3-phosphate oxidase, 2 U peroxidase, 2.7 mM p-chlorophenol, 0.04% Triton X-100 and 2 mM $MgSO_4.7H_2O$, and the glycerol content determined from the absorbance at 505 nm. For the determination of free fatty acids, 300 μl aliquots of the incubation mixture were added to 3 ml of chloroform/heptane (1:1 v/v) containing 2% (v/v) methanol. and the liberated free fatty acids determined with copper reagent and bathocuproine. The inhibitory activities of the cyclipostins were calculated from the combined results (glycerol and free fatty acid release) by plotting the log of the dose against the percent response (with the adenosine deaminase-induced lipolysis set at 100%). Data in the linear portion of the log (dose)-percent response curves were analyzed using parallel-line bioassay techniques.

| Antilipolytic effect: | |
| --- | --- |
| Example | IC$_{50}$[nM] |
| 1 | 5 |
| 2 | 20 |
| 4 | 100 |
| 6 | 10 |
| 7 | 5 |
| 10 | 100 |

The invention claimed is:

1. A compound according to formula (I)

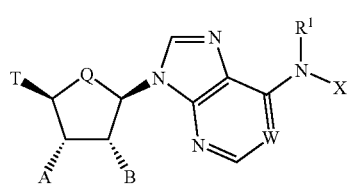

wherein:
W is N or N→O;
Q is CH$_2$;
R$^1$ is selected from the group consisting of hydrogen, C$_1$-C$_{10}$-alkyl, allyl, 2-methylallyl, 2-butenyl and C$_1$-C$_{10}$-cycloalkyl;
X is selected from the group consisting of

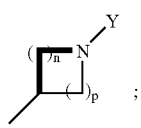 ; 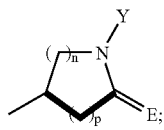

wherein n and p are independently 0, 1, 2, or 3, provided that n+p is at least 1;
and unsubstituted and at least monosubstituted C$_1$-C$_{10}$-alkylene-Y, C$_2$-C$_{10}$-alkenylene-Y, C$_3$-C$_{10}$-cycloalkylene-Y and C$_3$-C$_{10}$-cycloalkenylene-Y, the substituents of which are selected from the group consisting of halogens, CN, N$_3$, CF$_3$, C$_1$-C$_6$-alkyl and C$_1$-C$_6$-alkoxy;
E is O or S;
Y is selected from the group consisting of hydrogen; and unsubstituted and at least monosubstituted C$_1$-C$_{10}$-alkyl, aryl, heterocyclyl, aryl-(C$_1$-C$_{10}$-alkylene)- and heterocyclyl-(C$_1$-C$_{10}$-alkylene), the substituents of which are selected from the group consisting of halogens, CN, N$_3$, C$_1$-C$_6$-alkyl, C$_2$-C$_6$-alkenyl, C$_2$-C$_6$-alkynyl, aryl, heterocyclyl, C$_1$-C$_6$-alkoxy, NH$_2$, (C$_1$-C$_6$-alkyl)amino, di(C$_1$-C$_6$-alkyl)amino, C$_1$-C$_6$-alkoxy-(C$_1$-C$_6$-alkylene)-, nitro, carboxy, carbalkoxy, carboxy-(C$_1$-C$_6$-alkylene)-, carbalkoxy-(C$_1$-C$_6$-alkylene)-, hydroxy, hydroxy-(C$_1$-C$_6$-alkylene)-, mercapto, (C$_1$-C$_6$-alkyl)thio, mercapto-(C$_1$-C$_6$-alkylene)-, C$_1$-C$_6$-alkyl substituted by at least one halogen, (C$_1$-C$_6$-alkyl)sulfonyl-,aminosulfonyl-, (C$_1$-C$_6$-alkyl)aminosulfonyl-, (C$_1$-C$_6$-alkyl)sulfonylamido-, (C$_1$-C$_6$-alkyl)-sulfonyl-(C$_1$-C$_6$-alkylene)amino-, HO$_3$S—(C$_1$-C$_6$-alkylene)-, carbamoyl-(C$_1$-C$_6$-alkylene)-, (C$_1$-C$_6$-alkyl)-carbamoyl, (C$_1$-C$_6$-alkyl)-C(O)O—, (C$_1$-C$_6$-alkyl)-CO—, —SO$_3$H and carbamoyl;
T is a residue selected from the group consisting of C$_1$-C$_{10}$-alkyl, C$_1$-C$_{10}$-cycloalkyl, aryl-(C$_1$-C$_{10}$-alkylene)- and heterocyclyl-(C$_1$-C$_{10}$-alkylene), which residues are monosubstituted by halogen or OR$_2$, and which residues can be optionally substituted by at least one further substituent selected from the group consisting of halogens, CN, N$_3$, mercapto, NH$_2$, nitro, hydroxy, unsubstituted and at least monosubstituted C$_1$-C$_6$-alkyl, C$_1$-C$_6$-alkoxy, (C$_1$-C$_6$-alkyl)amino, (C$_1$-C$_6$-alkyl)thio, aryl and heterocyclyl, the substituents of which are selected from the group consisting of halogens, CN, N$_3$, C$_1$-C$_3$-alkyl, C$_1$-C$_3$-alkoxy and hydroxy;
R$^2$ is C$_1$-C$_{10}$-alkyl substituted by at least one halogen;
A is hydrogen, C$_1$-C$_{10}$-alkyl, hydroxy-(C$_1$-C$_{10}$-alkylene)-, C$_1$-C$_{10}$-alkoxy-(C$_1$-C$_{10}$-alkylene)-, or OR';
B ist hydrogen, C$_1$-C$_{10}$-alkyl, hydroxy-(C$_1$-C$_{10}$-alkylene)-, C$_1$-C$_{10}$-alkoxy-(C$_1$-C$_{10}$-alkylene)-, or OR";
R' and R" are independently selected from the group consisting of hydrogen, C$_1$-C$_6$-alkyl, aryl-(C$_1$-C$_6$-alkylene)-, (C$_1$-C$_6$-alkyl)-CO, carbalkoxy, aryl-(C$_1$-C$_6$-alkylene)-CO—, and aryl-O—CO—;
when A and B are OR' and OR", respectively, R' and R" together may form a substituent selected from the group consisting of

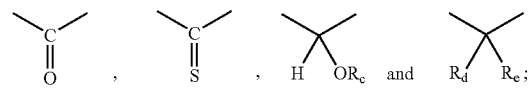

R$_C$ is hydrogen or C$_1$-C$_6$-alkyl;
R$_d$ and R$_e$ are independently hydrogen, C$_1$-C$_{10}$-alkyl, or together with the carbon atom to which they are attached may form a 1,1-cycloalkyl group;
heterocyclyl is a 4 to 10-membered, mono- or bicyclic heterocycle containing one or more heteroatoms selected from the group consisting of N, O and S;
aryl is phenyl, indan-1-yl, indan-2-yl, naphth-1-yl or naphth-2-yl;
or a pharmaceutically acceptable salt thereof, a pharmaceutically acceptable prodrug thereof, or an N-oxide thereof.

2. A compound according to claim 1, wherein in the formula (I)
W is N;
Q is CH$_2$;
R$^1$ is hydrogen or C$_1$-C$_6$-alkyl;
X is selected from the group consisting of

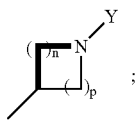 ;

and unsubstituted and at least monosubstituted C$_1$-C$_{10}$-alkylene-Y and C$_3$-C$_{10}$-cycloalkylene-Y, the substituents of which are selected from the group consisting of halogens, CN, $N_3$, $CF_3$, $C_1$-$C_6$-alkyl and $C_1$-$C_6$-alkoxy;

n+p is 3 or 4;

Y is selected from the group consisting of hydrogen; and unsubstituted and at least monosubstituted $C_1$-$C_{10}$-alkyl, aryl and heterocyclyl, the substituents of which are selected from the group consisting of halogens, CN $N_3$, $C_1$-$C_6$-alkyl, $C_1$-$C_6$-alkoxy, $NH_2$,($C_1$-$C_6$-alkyl)amino, di($C_1$-$C_6$-alkyl)amino, $C_1$-$C_6$-alkoxy-($C_1$-$C_6$-alkylene)-, nitro, carbox carbalkoxy, hydroxy, hydroxy-($C_1$-$C_6$-alkylene)-, mercapto, ($C_1$-$C_6$-alkyl)thio, mercapto-($C_1$-$C_6$-alkylene)-, $C_1$-$C_6$-alkyl substituted by at least one halogen, ($C_1$-$C_6$-alkyl)sulfonyl-, aminosulfonyl-; ($C_1$-$C_6$-alkyl)aminosulfonyl-, ($C_1$-$C_6$-alkyl)sulfonylamido-, $SO_3H$ and carbamoyl;

T is $C_1$-$C_{10}$-alkyl which is monosubstituted by halogen or $OR^2$, and which $C_1$-$C_{10}$-alkyl can furthermore be optionally substituted by at least one substituent selected from the group consisting of halogens, CN, $N_3$, mercapto, $NH_2$, nitro, hydroxy, unsubstituted and at least monosubstituted $C_1$-$C_6$-alkyl, $C_1$-$C_6$-alkoxy, ($C_1$-$C_6$-alkyl)amino, ($C_1$-$C_6$-alkyl)thio, aryl and heterocyclyl, the substituents of which are selected from the group consisting of halogens, CN, $N_3$, $C_1$-$C_3$-alkyl, $C_1$-$C_3$-alkoxy and hydroxy;

$R^2$ is $C_1$-$C_{10}$-alkyl substituted by at least one fluorine;

A is OR';

B is OR";

R' and R" are both hydrogen or R' and R" together form a substituent selected from the group consisting of

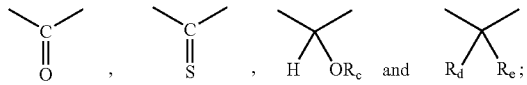

$R_c$ is hydrogen or methyl;

$R_d$ and $R_e$ are independently hydrogen, or $C_1$-$C_6$-alkyl;

heterocyclyl is selected from the group consisting of pyridyl, pyridazinyl, pyrimidinyl, isoquinolinyl, quinolinyl, quinazolinyl, imidazolyl, pyrrolyl, furanyl, thienyl, thiazolyl, benzothiazolyl, piperidinyl, pyrrolidinyl, tetrahydrofuranyl, tetrahydropyranyl, and morpholinyl;

aryl is phenyl, naphta-1-yl or naphtha-2-yl;

or a pharmaceutically acceptable salt thereof, a pharmaceutically acceptable prodrug thereof, or an N-oxide thereof.

3. A compound according to claim 1, wherein in the formula (I)

W is N;

Q is $CH_2$;

$R^1$ is hydrogen;

X is selected from the group consisting of

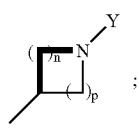

and unsubstituted and at least monosubstituted $C_1$-$C_6$-alkylene-Y, the substituents of which are selected from the group consisting of $CH_3$, $CH_3$—$CH_2$, Cl, F, $CF_3$ and $CH_3$—O;

n+p is 3 or 4;

Y is selected from the group consisting of unsubstituted and at least monosubstituted aryl and heterocyclyl, the substituents of which are selected from the group consisting of halogens, CN, $N_3$, $C_1$-$C_3$-alkyl, $C_1$-$C_3$-alkoxy, $NH_2$, ($C_1$-$C_3$-alkyl)amino, di($C_1$-$C_3$-alkyl)amino, $C_1$-$C_3$-alkoxy-($C_1$-$C_3$-alkylene)-, nitro, carboxy, hydroxy, hydroxy-($C_1$-$C_3$-alkylene)-, mercapto, ($C_1$-$C_3$-alkyl)thio, mercapto-($C_1$-$C_3$-alkylene)-, and $CF_3$;

T is $C_1$-$C_{10}$-alkyl substituted by at least one substituent selected from the group consisting of halogen and $OR^2$;

$R^2$ is $C_1$-$C_{10}$-alkyl substituted by at least one fluorine;

A and B are both hydroxy;

heterocyclyl is selected from the group consisting of pyridyl, pyridazinyl, pyrimidinyl, imidazolyl, thienyl, thiazolyl, benzothiazolyl, piperidinyl, pyrrolidinyl, tetrahydrofuranyl, and morpholinyl;

aryl is phenyl;

or a pharmaceutically acceptable salt thereof, a pharmaceutically acceptable prodrug thereof, or an N-oxide thereof.

4. A compound according to claim 1, wherein in the formula (I)

W is N;

Q is $CH_2$;

$R^1$ is hydrogen;

X is selected from the group consisting of

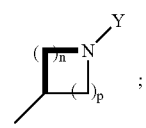

and unsubstituted and at least monosubstituted $C_1$-$C_6$-alkylene-Y the substituents of which are selected from the group consisting of $CH_3$, $CH_3$—$CH_2$, Cl, F, $CF_3$ and $CH_3$—O;

n+p is 3 or 4;

Y is selected from the group consisting of unsubstituted and at least monosubstituted phenyl, pyridyl and thienyl, the substituents of which are selected from the group consisting of halogens, $C_1$-$C_3$-alkyl, $C_1$-$C_3$-alkoxy, hydroxy, mercapto and $CF_3$;

T is fluoromethyl, trifluoromethoxymethyl or difluoromethoxymethyl;

A and B are both hydroxy;

or a pharmaceutically acceptable salt thereof, a pharmaceutically acceptable prodrug thereof, or an N-oxide thereof.

5. A compound according to claim 1, selected from the group consisting of:

(1R,2S,3R,5S)-3-{6-[1-(3-chloro-phenyl-1-yl)-pyrrolidin-3(S)-ylamino]-purin-9-yl}-5-fluoromethyl -cyclopentane-1,2-diol;

(1R,2S,3R,5S)-3-{6-[(R)-1-(3-chloro-thiophen-2-ylmethyl)-propylamino]-purin-9-yl}-5-fluoromethyl-cyclopentane-1,2-diol; and (1R,2S,3R,5R)-3-{6-[1-(3-chloro-phenyl-1-yl)-pyrrolidin-3(S)-ylamino]-purin-9-yl}-5-trifluoromethoxymethyl-cyclopentane-1,2-diol;

or a pharmaceutically acceptable salt thereof, a pharmaceutically acceptable prodrug thereof, or an N-oxide thereof.

6. A compound according to formula (III)

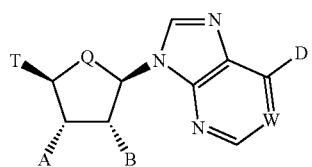

wherein:
W is N or N→O;
Q is CH$_2$;
D is halogen;
T is a residue selected from the group consisting of C$_1$-C$_{10}$-alkyl, C$_1$-C$_{10}$-cycloalkyl, aryl-(C$_1$-C$_{10}$-alkylene)- and heterocyclyl-(C$_1$-C$_{10}$-alkylene), which residues are monosubstituted by halogen or OR$_2$, and which residues can be optionally substituted by at least one substituent selected from the group consisting of halogens, CN, N$_3$, mercapto, NH$_2$, nitro, hydroxy, unsubstituted and at least monosubstituted C$_1$-C$_6$-alkyl, C$_1$-C$_6$-alkoxy, (C$_1$-C$_6$-alkyl)amino, aryl and heterocyclyl, the substituents of which are selected from the group consisting of halogens, CN, N$_3$, C$_1$-C$_3$-alkyl, C$_1$-C$_3$-alkoxy and hydroxy;
R$^2$ is selected from the group consisting of C$_1$-C$_{10}$-alkyl substituted by at least one substituent selected from halogens, C$_1$-C$_6$-alkyl-S(O)$_2$— and (C$_1$-C$_6$-alkyl)thio-C(S)—;
A is hydrogen, C$_1$-C$_{10}$-alkyl, hydroxy-(C$_1$-C$_{10}$-alkylene)-, C$_1$-C$_{10}$-alkoxy-(C$_1$-C$_{10}$-alkylene)-, or OR';
B ist hydrogen, C$_1$-C$_{10}$-alkyl, hydroxy-(C$_1$-C$_{10}$-alkylene)-, C$_1$-C$_{10}$-alkoxy-(C$_1$-C$_{10}$-alkylene)-, or OR";
R' and R" are independently selected from the group consisting of hydrogen, C$_1$-C$_6$-alkyl, aryl-(C$_1$-C$_6$-alkylene)-, (C$_1$-C$_6$-alkyl)-CO, carbalkoxy, aryl-(C$_1$-C$_6$-alkylene)-CO—, and aryl-O—CO—;
when A and B are OR' and OR", respectively, R' and R" together may form a substituent selected from the group consisting of

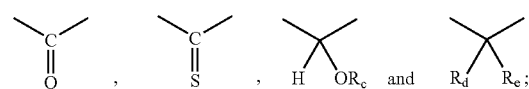

R$_C$ is hydrogen or C$_1$-C$_6$-alkyl;
R$_d$ and R$_e$ are independently hydrogen, C$_1$-C$_{10}$-alkyl, or together with the carbon atom to which they are attached may form a 1,1-cycloalkyl group;
heterocyclyl is a 4 to 10-membered, mono- or bicyclic heterocycle containing one or more heteroatoms selected from the group consisting of N, O and S;
aryl is phenyl, indan-1-yl, indan-2-yl, naphth-1-yl or naphth-2-yl;
or a pharmaceutically acceptable salt thereof, a pharmaceutically acceptable prodrug thereof, or an N-oxide thereof.

7. A compound according to claim 6, wherein in the formula (III)
W is N;
Q is CH$_2$;
D is chlorine or fluorine;

T is fluoromethyl, trifluoromethoxymethyl, difluoromethoxymethyl, CH$_3$SC(S)—O—CH$_2$— or CH$_3$S(O)$_2$—O—CH$_2$—;
A is OR';
B is OR";
R' and R" are hydrogen or R' and R" together form a substituent selected from the group consisting of

R$_C$ is hydrogen or C$_1$-C$_3$-alkyl;
R$_d$ and R$_e$ are independently hydrogen or C$_1$-C$_3$-alkyl;
or a pharmaceutically acceptable salt thereof, a pharmaceutically acceptable prodrug thereof, or an N-oxide thereof.

8. A compound according to claim 6, selected from the group consisting of:
6-chloro-9-((3aS,4R,6S,6aR)-6-fluoromethyl-2,2-dimethyl-tetrahydro-cyclopenta-1,3-dioxol-4-yl) -9H-purine; 6-fluoro-9-((3aS,4R,6S,6aR)-6-fluoromethyl-2,2-dimethyl -tetrahydro-cyclopenta-1,3-dioxol-4-yl)-9H-purine; 6-chloro-9-((1R,2S,3R,5R)-5-fluoro-methyl-1,2-dihydroxy-cyclopent-3-yl-) -9H-purine; 6-fluoro-9-((1R,2S,3R,5R)-5-fluoro-methyl-1,2-dihydroxy-cyclopent-3-yl-)-9H-purine; 6-chloro-9-((3aS,4R,6S,6aR)-6-trifluoromethoxymethyl-2,2-dimethyl-tetrahydro-cyclopenta-1,3-dioxol-4-yl)-9H-purine; 6-fluoro-9-((3aS,4R,6S,6aR)-6-trifluoromethoxymethyl -2,2-dimethyl-tetrahydrocyclopenta-1,3-dioxol-4-yl)-9H-purine; 6-chloro-9-((1R,2S,3R,5R)-5-trifluoromethoxy-methyl-1,2-dihydroxy-cyclopent-3-yl-)-9H-purine and 6-fluoro-9-((1R,2S,3R,5R)-5-trifluoromethoxymethyl-1,2-dihydroxy-cyclopent-3-yl-)-9H-purine, or a pharmaceutically acceptable salt thereof, a pharmaceutically acceptable prodrug thereof or an N-oxide thereof.

9. A method for the treatment of a disease chosen from the group consisting of insulin resistance, type 2 diabetes, or for providing an anti-lipolytic effect, which method comprises the administration of a physiologically active amount of a compound as defined in claim 1 or a pharmaceutically acceptable salt thereof, a pharmaceutically acceptable prodrug thereof or an N-oxide thereof.

10. The method according to claim 9 for the treatment of a disease chosen from the group consisting of insulin resistance and type 2 diabetes.

11. A pharmaceutical preparation comprising a pharmaceutically acceptable carrier and an effective dose of at least one compound of the formula (I) as defined in claim 1 or a pharmaceutically acceptable salt thereof, a pharmaceutically acceptable prodrug thereof or an N-oxide thereof.

12. A pharmaceutical preparation according to claim 11, which pharmaceutical preparation is in the form of a pill, tablet, lacquered tablet, sugar-coated tablet, suckable tablet, granule, capsule, hard or soft gelatin capsule, aqueous, alcoholic or oily solution, syrup, emulsion or suspension, suppository, solution for injection or infusion, ointment, tincture, cream, lotion, powder, spray, transdermal therapeutic systems, nasal spray, aerosol mixture, microcapsule, implant, rod or plaster.

13. A method for the synthesis of a compound according to claim 1 which method comprises reacting the respective 6-chloropurine and/or 6-fluoropurine with an appropriate amine.

14. A method for the treatment of a disease chosen from the group consisting of insulin resistance, type 2 diabetes, or for providing an anti-lipolytic effect, which method comprises the administration of a pharmaceutical preparation comprising a pharmaceutically acceptable carrier and an effective dose of at least one compound of the formula (I) as defined in claim 1 or a pharmaceutically acceptable salt thereof, a pharmaceutically acceptable prodrug thereof or an N-oxide thereof.

* * * * *